US011439686B2

(12) United States Patent
Arce Saez et al.

(10) Patent No.: US 11,439,686 B2
(45) Date of Patent: Sep. 13, 2022

(54) RECOMBINANT FSH COMPOSITION FOR TREATMENT OF INFERTILITY

(71) Applicant: FERRING B.V., Hoofddorp (NL)

(72) Inventors: Joan Carles Arce Saez, Copenhagen (DK); Lisbeth Helmgaard, Copenhagen (DK); Bjarke Mirner Klein, Copenhagen (DK)

(73) Assignee: FERRING B.V., Hoofddorp (NL)

( * ) Notice: Subject to any disclaimer, the term of this patent is extended or adjusted under 35 U.S.C. 154(b) by 62 days.

(21) Appl. No.: 16/881,163

(22) Filed: May 22, 2020

(65) Prior Publication Data

US 2020/0353053 A1 Nov. 12, 2020

Related U.S. Application Data

(63) Continuation of application No. 15/566,657, filed as application No. PCT/EP2016/058358 on Apr. 15, 2016, now Pat. No. 10,660,938.

(30) Foreign Application Priority Data

Apr. 17, 2015 (EP) .................................... 15164043

(51) Int. Cl.
*A61K 38/24* (2006.01)
*A61P 5/06* (2006.01)
*A61P 5/24* (2006.01)

(52) U.S. Cl.
CPC ................ *A61K 38/24* (2013.01); *A61P 5/06* (2018.01); *A61P 5/24* (2018.01)

(58) Field of Classification Search
None
See application file for complete search history.

(56) References Cited

U.S. PATENT DOCUMENTS 8,173,592 B1 5/2012 Engel et al.
10,660,938 B2 5/2020 Arce Saez et al.

FOREIGN PATENT DOCUMENTS

RU 2226395 C2 7/2003
WO WO-2013/020996 A1 2/2013

OTHER PUBLICATIONS

Zalata et al., Andrologia, 2008; 40: 392-397 (Year: 2008).*
The abstract by Salim et al., Human Fertility, (Jun. 2011) vol. 14, No. 2, pp. 63. Abstract No. P086 (Year: 2011).*
Chin et al., "Biological activity and metabolic clearance of recombinant human follicle stimulating hormone produced in Sp2/0 myeloma cells," Cytotechnology, 1996; 21: 171-182.
Falconer et al., "Follicle-Stimulating Hormone Receptor Polymorphisms in a Population of Infertile Women," Acta Obstetricia et Gynecologica Scandinavica (Aug. 2005) vol. 84, No. 8, pp. 806-811.
Kallio et al., "Anti-Mullerian Hormone as a Predictor of Follicular Reserve in Ovarian Insufficiency: Special Emphasis on FSH-Resistant Ovaries," Human Reproduction (Jan. 2012) vol. 27, No. 3, pp. 854-860.
Lekamge et al., J Assist Reprod Genet. 2008; 25:515-521.
Loutradis et al., "FSH Receptor Gene Polymorphisms Have a Role for Different Ovarian Response to Stimulation in Patients Entering IVF/ICSI-ET Programs," Journal of Assisted Reproduction and Genetics, (Apr. 2006) vol. 23, No. 4, pp. 177-184.
Mayorga et al., "Ovarian Response to Follicle-Stimulating Hormone (FSH) Stimulation Depends on the FSH Receptor Genotype," The Journal of Clinical Endocrinology & Metabolism, vol. 85, No. 9, pp. 3365-3369 (2000).
Nelson et al.,"Ati-Müllerian hormone-based approach to controlled ovarian stimulatrion for assisted conception," Human Reproduction, 2009, 24: 867-875 (2009).
Office Action dated Jan. 7, 2020 in Japanese Application No. 2017-554631.
Office Action dated Jun. 25, 2019 in Russian Application No. 2017128296/04(048818).
Search Report dated Jun. 20, 2019 in Russian Application No. 2017128296/04(048818).
Sheikha et al., "Investigating the association between polymorphism of follicle-stimulating hormone receptor gene and ovarian response in controlled ovarian hyperstimulation," J. Human Reprod Sci. 2011; 4: 86-90; printable version available from https://www.ncbi.nlm.nih.gov/pmc/articles/PMC3205539/?report=printable; 13 pages.
Simoni et al., "Isoforms and Single Nucleotide Polymorphisms of the FSH Receptor Gene: Implications for Human Reproduction," Human Reproduction Update (Sep. 2002) vol. 8, No. 5, pp. 413-421.
Simoni et al., "Mutational Analysis of the Follicle-Stimulating Hormone (FSH) Receptor in Normal and Infertile Men: Identification and Characterization of Two Discrete FSH Receptor Isoforms," Journal of Clinical Endocrinology and Metabolism (Feb. 1999) vol. 84, No. 2. pp. 751-755.
Wunsch et al., "Polymorphism of the FSH Receptor and Ovarian Response to FSH," Annales D'Endocrinologie (Jun. 2007) vol. 68, No. 2-3, pp. 160-166.

* cited by examiner

*Primary Examiner* — Christina M Borgeest
(74) *Attorney, Agent, or Firm* — Foley & Lardner LLP

(57) ABSTRACT

Preparations including FSH, for example recombinant FSH, for use in the treatment of infertility.

10 Claims, 5 Drawing Sheets
Specification includes a Sequence Listing.

Figs 1, 2 and 3: Plasmid maps of the pFSHalpha/beta ,pST3 and pST6 expression vectors. CMV = Cytomegalovirus promoter, BGHp(A) = Bovine Growth Hormone poly-adenylation sequence, fl ori = fl origin of replication, SV40 = Simian Virus 40 promoter, Neo = Neomycin resistance marker, Hyg = Hygromycin resistance marker, SV40 p(A) = Simian Virus 40 poly-adenylation sequence, FSH A = Follicle stimulating hormone alpha polypeptide, FSH B = Follicle stimulating hormone beta polypeptide, ST3GAL4 = α2,3-sialyltransferase, ST6GAL1 = α2,6-sialyltransferase, ColEI = ColEI origin of replication, Amp = ampicillin resistance marker.

Figure 1. FSH expression vector

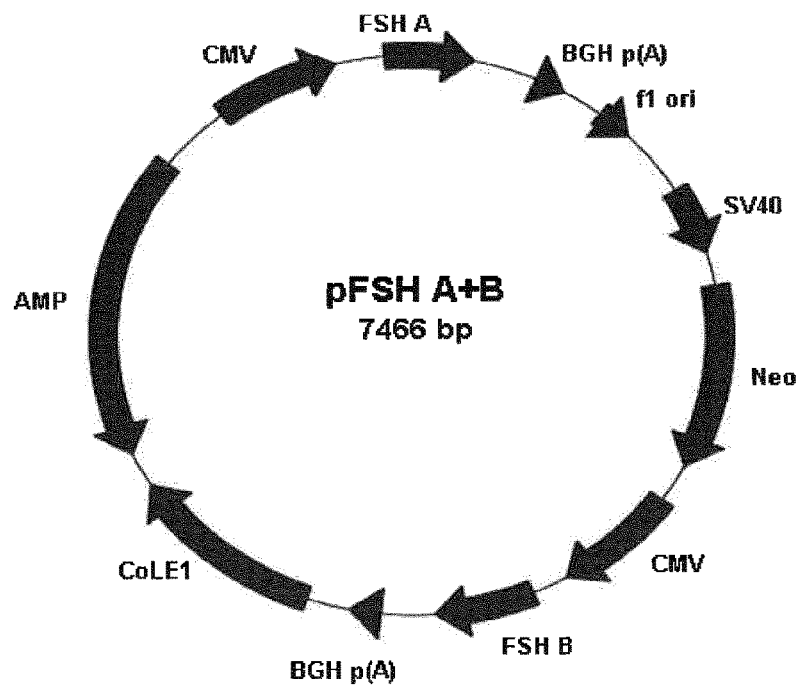

Figure 2. α2,3-sialyltransferase (ST3GAL4) expression vector
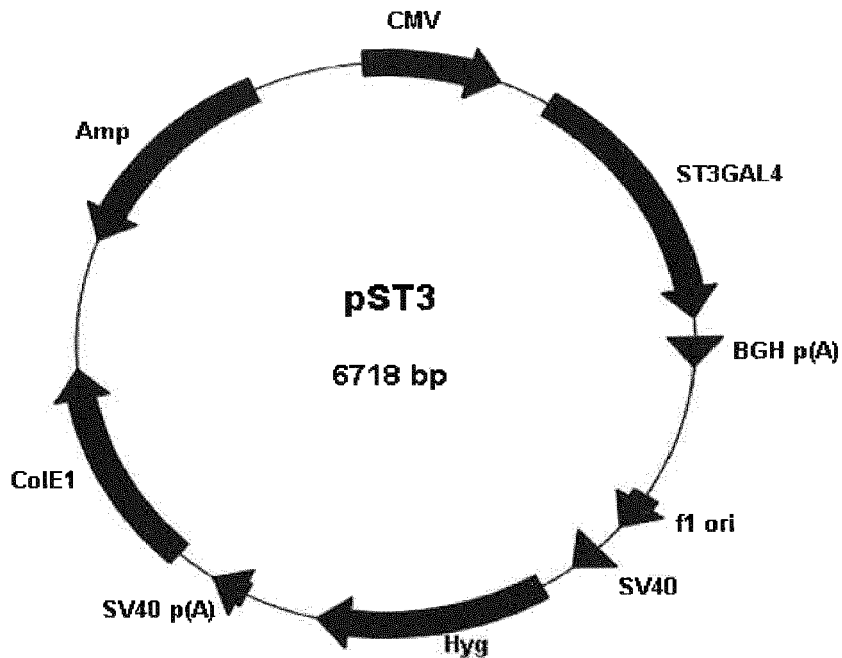
Figure 3. α2,6-sialyltransferase (ST6GAL1) expression vector
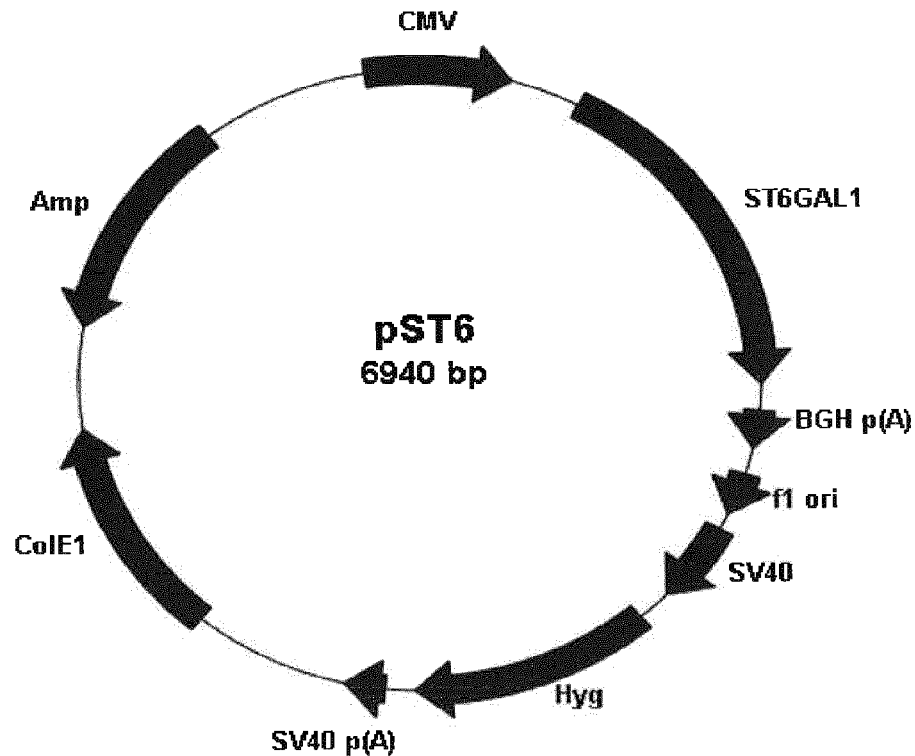

Frequency of SNP FSH-R (-29,307,680)
A-Thr-Asn/A-Thr-Asn  3%
A-Thr-Asn/A-Ala-Ser  3%
A-Ala-Ser/A-Ala-Ser  1%
A-Thr-Asn/G-Thr-Asn  10%
A-Thr-Asn/G-Ala-Ser  20%
A-Ala-Ser/G-Ala-Ser  5%
G-Thr-Asn/G-Thr-Asn  16%
G-Thr-Asn/G-Ala-Ser  30%
G-Ala-Ser/G-Ala-Ser  11%

Fig 6

Exposure to IMP
Data: FE 999049 C00009 / Full analysis set / low AMH stratum

Stratum: Low AMH

|  | SER/SER | SER/ASN | ASN/ASN | p-value*a | P-values*b Dose Group | P-values*b SNP Group |
|---|---|---|---|---|---|---|
| Full Analysis Set | 16 | 58 | 39 |  |  |  |
| Duration of gonadotropin treatment (days) |  |  |  |  |  |  |
| N | 16 | 58 | 39 | 0.057 | 0.086 | 0.026 |
| Mean | 9.31 | 8.21 | 8.28 |  |  |  |
| SD | 1.89 | 1.69 | 2.08 |  |  |  |
| Median | 9 | 8 | 8 |  |  |  |
| Minimum | 6 | 5 | 1 |  |  |  |
| Maximum | 13 | 12 | 14 |  |  |  |

*a: P-value is calculated from Kruskal-Wallis test comparing the SNP groups.
*b: P-values are calculated from a linear model (Duration of IMP or Total Dose of IMP = Dose + SNP Group).

FE999049/ART/000009/08APR2015-BEMK/STAT MISC/SNP/EXP_IMP_SNP.SAS

Fig 7

Duration of stimulation: Linear model including treatment dose and SNP as factors
Data: FE 999049 000009 / Full analysis set / low AMH stratum

| AMH stratum | Factor | Level | LS means | SE | 95% CI Lower | 95% CI Upper | P-value |
|---|---|---|---|---|---|---|---|
| Low AMH (5.0-14.9 pmol/L) | DOSE | | | | | | 0.086 |
| | SNP | | | | | | 0.026 |
| | SNP | ASN/ASN | 8.13 | 0.30 | 7.54 | 8.72 | |
| | | SER/ASN | 8.26 | 0.24 | 7.78 | 8.74 | |
| | | SER/SER | 9.59 | 0.47 | 8.66 | 10.51 | |

SE = Standard error of the estimate
CI = Confidence interval
P-value based on F-test S:\FCDB\FE999049\ART\000009\Report\Stat_Misc\SNP\EXP_IMP_SNP_II.sas     bemk/08APR15

RECOMBINANT FSH COMPOSITION FOR TREATMENT OF INFERTILITY

CROSS-REFERENCE TO RELATED APPLICANTS

The present application is a continuation of U.S. application Ser. No. 15/566,657, filed Oct. 13, 2017 (now U.S. Pat. No. 10,660,938), which is the U.S. National Stage of International Application PCT/EP2016/058358, filed Apr. 15, 2016, and claims priority to European Patent Application No. 15164043.0, filed Apr. 17, 2015.

SEQUENCE LISTING

The instant application contains a Sequence Listing which has been submitted electronically in ASCII format and is hereby incorporated by reference in its entirety.

The present invention relates to compositions and pharmaceutical products for the treatment of infertility.

Assisted reproductive technology (ART) techniques such as in vitro fertilisation (IVF) are well known. These ART techniques generally require a step of controlled ovarian stimulation (COS), in which a cohort of follicles is stimulated to full maturity. Standard COS regimens include administration of gonadotrophins, such as follicle stimulating hormone (FSH) alone or in combination with luteinising hormone (LH) activity to stimulate follicular development, normally with administration of a GnRH analogue prior to and/or during stimulation to prevent premature LH surge. The pharmaceutical compositions generally used for COS include recombinant follicle stimulating hormone (rFSH), urinary derived FSH, recombinant FSH+LH preparations, urinary derived menotrophin [human menopausal gonadotrophin (hMG)] and highly purified human menopausal gonadotrophin (HP-hMG). IVF can be associated with a risk of ovarian hyperstimulation syndrome (OHSS), which can be life threatening in severe cases.

As indicated above, standard COS protocols generally involve administration of FSH. The dose of FSH generally depends on a number of factors, including age, any previous response to FSH stimulation, basal level of FSH, antral follicle count and more recently anti-Müllerian hormone (AMH). The clinician will expect ovarian multifollicular development in response to a given dose, together with a rise in circulating 17-β-estradiol.

If the response (ovarian multifollicular development, rise in circulating 17-β-estradiol) to a given dose is adequate or as expected, this indicates normal ovarian function, which is also referred to as normal ovarian reserve. Patients who do not respond well to FSH stimulation produce few follicles, and consequently their 17-β-estradiol levels during stimulation rise slowly and reach comparatively low levels. These patients are referred to as "low responders", and may be said to have a diminished ovarian reserve. Several factors are believed to be involved in low response, including increasing age, pelvic adhesions, ovarian disease and immunological factors.

The ability to predict the response potential of women to controlled ovarian stimulation (COS) may allow the development of individualised COS protocols. This could, for example, reduce the risk of OHSS in women predicted to have an excessive response to stimulation, improve pregnancy outcomes in women classed as poor responders, and/or lead to reduced dose of (and exposure to) FSH and therefore reduced cost of therapy (and increased safety of therapy) in specific patients.

The serum concentration of anti-Müllerian hormone (AMH) is now established as a reliable marker of ovarian reserve. Decreasing levels of AMH are correlated with reduced ovarian response to gonadotrophins during COS. Further, high levels of AMH are a good predictor of excessive ovarian response, and an indicator of risk of OHSS.

In a preliminary study of women under 35 years old undergoing ART, the CONSORT dosing algorithm (incorporating basal FSH, BMI, age and AFC) was used to predict the optimal FSH starting dose for COS in women at risk of developing OHSS (Olivennes et. al., 2009). Individualising the dose did lead to adequate oocyte yield and good pregnancy rate. However, there were high rates of cancellations in the low dose group (75 IU FSH) due to inadequate response, and OHSS did occur in a significant proportion of the patients.

As indicated above, standard COS protocols may include administration of FSH. FSH is naturally secreted by the anterior pituitary gland and functions to support follicular development and ovulation. FSH comprises a 92 amino acid alpha sub-unit, also common to the other glycoprotein hormones LH and CG, and a 111 amino acid beta sub-unit unique to FSH that confers the biological specificity of the hormone (Pierce and Parsons, 1981). Each sub-unit is post translationally modified by the addition of complex carbohydrate residues. Both subunits carry 2 sites for N-linked glycan attachment, the alpha sub-unit at amino acids 52 and 78 and the beta sub-unit at amino acid residues 7 and 24 (Rathnam and Saxena, 1975, Saxena and Rathnam, 1976). FSH is thus glycosylated to about 30% by mass (Dias and Van Roey. 2001. Fox et al. 2001).

FSH purified from post-menopausal human urine has been used for many years in infertility treatment; both to promote ovulation in natural reproduction and to provide oocytes for assisted reproduction technologies. The currently approved recombinant FSH (rFSH) products for ovarian stimulation, such as follitropin alfa (GONAL-F, Merck Serono/EMD Serono) and follitropin beta (PUREGON/FOLLISTIM, MSD/Schering-Plough), are derived from a Chinese Hamster Ovary (CHO) cell line. Currently, no rFSH products from a human cell line are commercially available.

There is considerable heterogeneity associated with FSH preparations which relates to differences in the amounts of various isoforms present. Individual FSH isoforms exhibit identical amino acid sequences but differ in the extent to which they are post-translationally modified; particular isoforms are characterised by heterogeneity of the carbohydrate branch structures and differing amounts of sialic acid (a terminal sugar) incorporation, both of which appear to influence the specific isoform bioactivity.

Glycosylation of natural FSH is highly complex. The glycans in naturally derived pituitary FSH can contain a wide range of structures that can include combinations of mono-, bi-, tri- and tetra-antennary glycans (Pierce and Parsons, 1981. Ryan et al., 1987. Baenziger and Green, 1988). The glycans can carry further modifications: core fucosylation, bisecting glucosamine, chains extended with acetyl lactosamine, partial or complete sialylation, sialylation with α2,3 and α2,6 linkages, and sulphated galactosamine substituted for galactose (Dalpathado et al., 2006). Furthermore, there are differences between the distributions of glycan structures at the individual glycosylation sites. A comparable level of glycan complexity has been found in FSH derived from the serum of individuals and from the urine of post-menopausal women (Wide et al., 2007).

The glycosylation of recombinant FSH products reflects the range of glycosyl-transferases present in the host cell line. The commercially available rFSH products are derived from engineered Chinese hamster ovary cells (CHO cells). The range of glycan modifications in CHO cell derived rFSH are more limited than those found on the natural products. Examples of the reduced glycan heterogeneity found in CHO cell derived rFSH include a lack of bisecting glucosamine and a reduced content of core fucosylation and acetyl lactosamine extensions (Hard et al., 1990). In addition, CHO cells are only able to add sialic acid using the α2,3 linkage (Kagawa et al, 1988, Takeuchi et al, 1988, Svensson et al., 1990); CHO cell derived rFSH only includes α2,3-linked sialic acid and does not include α2,6-linked sialic acid.

Thus CHO cell derived FSH is different from naturally produced FSH (e.g. human Pituitary/serum/urinary FSH) which contains glycans with a mixture of α2,3 and α2,6-linked sialic acid, with a predominance of the former. Thus, recombinant proteins expressed using the CHO system will differ from their natural counterparts in their type of terminal sialic acid linkages. This is an important consideration in the production of biologicals for pharmaceutical use since the carbohydrate moieties may contribute to the pharmacological attributes of the molecule.

The present applicants have developed a human derived recombinant FSH which is the subject of International Patent Application No. PCT/GB2009/000978, published as WO2009/127826A. Recombinant FSH with a mixture of both α2,3 and α2,6-linked sialic acid was made by engineering a human cell line to express both rFSH and α2,3 sialyltransferase. The expressed product is highly acidic and carries a mix of both α2,3- and α2,6-linked sialic acids; the latter provided by the endogenous sialyl transferase activity. It was found that the type of sialic acid linkage, α2,3- or α2,6-, can have a dramatic influence on biological clearance of FSH. Recombinant FSH with a mixture of both α2,3 and α2,6-linked sialic acid has two advantages over rFSH expressed in conventional CHO cells: first the material is more highly sialylated due to the combined activities of the two sialyltransferases; and secondly the material more closely resembles the natural FSH. This is likely to be more biologically appropriate compared to CHO cell derived recombinant products that have produce only α2,3 linked sialic acid (Kagawa et al, 1988, Takeuchi et al, 1988, Svensson et al., 1990) and have decreased sialic acid content (Ulloa-Aguirre et al. 1995, Andersen et al. 2004).

Recently, it has been suggested that the follicle-stimulating hormone receptor or FSH receptor (FSHR) may be related to or involved in diminished ovarian reserve. The FSH receptor is a transmembrane receptor that interacts with FSH. The FSH receptor is G-protein-coupled 7-transmembrane receptor linked to adenylate cyclase, with a large N-terminal ligand-binding domain and a C-terminal cytoplasmic tail rich in serine and threonine residues as putitive phosphorylation sites. Its activation is necessary for the hormonal functioning of FSH. It has been postulated that mutations in the FSH receptor might lead to a diminished ovarian reserve. As well as mutations, FSH receptor variants (FSH receptor polymorphisms) are found. Two such polymorphisms are located at position 307 (Ala/Thr) and position 680 (Asn/Ser) in exon 10 of the FSH receptor (FIG. 4). These are variant Ala or Thr in position 307, and Asn or Ser in position 680. These polymorphisms lead to three distinct FSH receptor genotypes with regard to position 680: Asn/Asn, Asn/Ser and Ser/Ser [see Simoni et al, Journal of Clinical Endocrinology and Metabolism, Vol 84, No. 2, 751-755 (1999), Falconer et al, Acta Obstet Gynecol Scand 2005: 84: 806-811 (2005), and Loutradis et al, Journal of Assisted Reproduction and Genetics, Vol. 23, No. 4, (April 2006)].

The present applicants have found that patients identified as having low AMH [AMH level <15 pmol/L, who would generally be associated with a low response], as well as having variant Ser/Ser at position 680 of the FSH receptor, have a longer duration of FSH treatment, compared to patients with low AMH and variant Asn/Asn or variant Asn/Ser at position 680 of the FSH receptor. An increased starting FSH dose to patients having low AMH [AMH level <15 pmol/L, (e.g. 0.05 pmol/L to 14.9 pmol/L, e.g. 5.0 pmol/L to 14.9 pmol/L)], as well as having variant Ser/Ser at position 680 of the FSH receptor, may therefore be an alternative to avoid the longer duration of FSH treatment. This allows tailoring of the dose of FSH in specific patients identified as having specific AMH level, as well as specific polymorphism at the FSHR.

Administration of a higher starting dose of FSH to patients having low AMH [AMH level <15 pmol/L, (e.g. 0.05 pmol/L to 14.9 pmol/L, e.g. 5.0 pmol/L to 14.9 pmol/L)], as well as having variant Ser/Ser at position 680 of the FSH receptor, is advantageous because it may provide increased probability of success (in terms of pregnancy and/or live birth) and better predictability of success. Success is more likely if the patient has an adequate response (expected ovarian multifollicular development, rise in circulating 17-β-estradiol) occurring within an ideal treatment window. Success is further enhanced if the response is within the centre of this treatment window; that is, not too early in the window and not too late. Reduction of the duration of treatment in patients having low AMH and variant Ser/Ser at position 680 of the FSH receptor (by increasing the dose above 12 μg) may bring the response towards the centre of the treatment window, with enhanced likelihood of success.

According to the present invention in a first aspect there is provided a composition (e.g. a pharmaceutical composition) for use in the treatment of infertility, the composition comprising 9 to 24 μg follicle stimulating hormone (FSH), wherein the composition is for (e.g. daily) administration to a patient identified as (e.g. selected as) having variant Ser/Ser at position 680 of the FSH receptor (prior to treatment). The composition may be for (e.g. daily) administration to a patient identified as (e.g. selected as) having variant Ser/Ser at position 680 of the FSH receptor and identified as (e.g. selected as) having a serum AMH level <15 pmol/L (e.g. 0.05 pmol/L to 14.9 pmol/L) (prior to treatment). The composition may comprise 9 to 24 μg FSH, for example 10 to 18 μg FSH, for example 12 to 16 μg FSH, for example 12 to 15 μg FSH. The composition may comprise >12 μg FSH, for example 12.3 to 24 μg FSH, for example 12.33 to 24 μg FSH, for example 12.67 to 24 μg FSH, for example 13 to 24 μg FSH, for example 13 to 16 μg FSH, for example 13 to 15 μg FSH.

The composition (e.g. pharmaceutical composition) may comprise a daily dose of, or a daily dose equivalent to, the amounts of human derived rFSH defined above, herein, and in the claims. The composition (e.g. pharmaceutical composition) may be for (daily) administration of FSH starting on day one of treatment and continuing for six to sixteen days, for example seven to sixteen days, for example 8 to 16 days, for example 8 to 13 days. The treatment of infertility may comprise a step of identifying (e.g. determining, e.g. measuring) the variant at position 680 of the FSH receptor of the patient; and a step of administering the dose to a patient (identified as) having variant Ser/Ser at position 680 of the FSH receptor. The treatment of infertility may comprise a step of identifying (e.g. determining, e.g. measuring) the serum AMH level of the patient, and administering the dose to a patient (identified as) having serum AMH level of <15 pmol/L (e.g. 0.05 pmol/L to 14.9 pmol/L).

The FSH may be recombinant FSH. The FSH may be recombinant FSH including α2,3- and α2,6-sialylation. The FSH may be recombinant FSH including α2,3- and α2,6-sialylation wherein 1 to 99% of the total sialylation is α2,6-sialylation and 99% to 1% of the total sialylation is α2,3-sialylation. The FSH may be recombinant FSH including α2,3- and α2,6-sialylation wherein 1 to 50% of the total sialylation is α2,6-sialylation and 50% to 99% of the total sialylation is α2,3-sialylation. The FSH may be recombinant FSH including α2,3- and α2,6-sialylation wherein 5 to 40% of the total sialylation is α2,6-sialylation and 60% to 95% of the total sialylation is α2,3-sialylation. Preferably the FSH is a human cell line derived recombinant FSH.

According to the present invention in a further aspect there is provided a composition (e.g. a pharmaceutical composition) comprising follicle stimulating hormone (FSH) for use in the treatment of infertility in a patient having a serum AMH level <15 pmol/L (e.g. 0.05 pmol/L to 14.9 pmol/L) and having variant Ser/Ser at position 680 of the FSH receptor, wherein the composition is to be administered at a dose of or equivalent to 9 to 24 μg recombinant FSH per day; and wherein the treatment of infertility comprises a step of identifying (e.g. determining) the serum AMH level of the patient; a step of identifying the variant at position 680 of the FSH receptor of the patient; and a step of administering the composition to a patient (identified as) having a serum AMH level <15 pmol/L (e.g. 0.05 pmol/L to 14.9 pmol/L) and variant Ser/Ser at position 680 of the FSH receptor. The composition may comprise 9 to 24 μg FSH, for example 10 to 18 μg FSH, for example 12 to 16 μg FSH, for example 12 to 15 μg FSH. The composition may comprise >12 μg FSH, for example 12.3 to 24 μg FSH, for example 12.33 to 24 μg FSH, for example 12.67 to 24 μg FSH, for example 13 to 24 μg FSH, for example 13 to 16 μg FSH, for example 13 to 15 μg FSH.

The composition (e.g. a pharmaceutical composition) may be for use in the treatment of infertility in a patient having a serum AMH level <15 pmol/L (e.g. 0.05 pmol/L to 14.9 pmol/L) and having variant Ser/Ser at position 680 of the FSH receptor [wherein the treatment of infertility comprises a step of identifying (e.g. determining) the serum AMH level of the patient; a step of identifying the variant at position 680 of the FSH receptor of the patient; and a step of administering the dose to a patient (identified as) having a serum AMH level <15 pmol/L (e.g. 0.05 pmol/L to 14.9 pmol/L) and variant Ser/Ser at position 680 of the FSH receptor].

The FSH may be recombinant FSH. The FSH may be recombinant FSH including α2,3- and α2,6-sialylation. The FSH may be recombinant FSH including α2,3- and α2,6-sialylation wherein 1 to 99% of the total sialylation is α2,6-sialylation and 99% to 1% of the total sialylation is α2,3-sialylation. The FSH may be recombinant FSH including α2,3- and α2,6-sialylation wherein 1 to 50% of the total sialylation is α2,6-sialylation and 50% to 99% of the total sialylation is α2,3-sialylation. The FSH may be recombinant FSH including α2,3- and α2,6-sialylation wherein 5 to 40% of the total sialylation is α2,6-sialylation and 60% to 95% of the total sialylation is α2,3-sialylation. Preferably the FSH is a human cell line derived recombinant FSH.

The dose provides an effective response while minimising risk of OHSS.

The doses above may be for treatment of infertility in the patient's (subject's) first stimulation protocol. It will be appreciated that for further stimulation cycles, the doses may be adjusted according to actual ovarian response in the first cycle.

The rFSH may be present as a single isoform or as a mixture of isoforms.

The applicants have devised "individualised" COS protocols wherein specific doses of recombinant FSH are used to treat patients based on their specific AMH levels and FSHR single nucleotide polymorphism, thereby increasing the likelihood of adequate response to stimulation (e.g. in patients having a low response potential), and/or decreased risk of OHSS or other side effect.

The serum level of AMH may be determined (e.g. measured) by any method known in the art. As an example, the serum AMH level is measured using the AMH Gen-II enzyme linked immunosorbent assay, a kit (Beckman Coulter, Inc., Webster, Tex.). This assay can detect AMH concentrations greater than 0.57 pmol/L with a minimum limit of quantitation of 1.1 pmol/L. Other assays may be used. Herein, serum AMH values are generally recited in terms of pmol/L. This may be converted to ng/mL using the conversion equation ng/ml AMH=7.1 pmol/L AMH. Thus, the composition may be for (e.g. daily) administration to a patient identified as (e.g. selected as) having a serum AMH level <15 pmol/L (e.g. 0.05 pmol/L to 14.9 pmol/L) when measured using a Beckmann-Coulter Gen-II enzyme linked immunosorbent assay or a comparable AMH level measured by a different method.

Herein the terms "patient" and "subject" are used interchangeably.

The composition (e.g. pharmaceutical composition) preferably comprises a daily dose of, or a daily dose equivalent to, the amounts of human derived rFSH defined above, herein, and in the claims. The (daily) dose may be an initial dose (i.e. it may be reduced, increased, or maintained during the treatment).

The patient identified as having variant Ser/Ser at position 680 of the FSH receptor may be identified by means well known in the art, for example by identification of the allelic variant at position 680 of the FSH receptor following extraction of genomic DNA by methods well known in the art [e.g. by means of a kit for extraction of genomic DNA from blood, and subsequent DNA sequencing, as described in e.g. Gromoll et al, Methods, 21, 83-97 (2000), Simoni et al, Journal of Clinical Endocrinology and Metabolism, Vol 84, No. 2, 751-755 (1999), Falconer et al, Acta Obstet Gynecol Scand 2005: 84: 806-811 (2005), and references therein, or DNA extraction followed by single strand conformation polymorphism (SSCP followed by gel electrophoresis etc.), or by a PCR and RFLP method such as that set out in Loutradis et al, Journal of Assisted Reproduction and Genetics, Vol. 23, No. 4, April 2006)]. Thus, the composition may be for (e.g. daily) administration to a patient identified as (e.g. selected as) having variant Ser/Ser at position 680 of the FSH receptor when measured by extraction of genomic DNA (e.g. from blood) and subsequent analysis by PCR and RFLP methods such as that set out in Loutradis et al, Journal of Assisted Reproduction and Genetics, Vol. 23, No. 4, April 2006, or comparable method.

The composition (e.g. pharmaceutical composition) may be for (daily) administration of FSH starting on day one of treatment and continuing for six to sixteen days, for example seven to sixteen days, for example 8 to 16 days, for example 8 to 13 days. The composition (e.g. pharmaceutical composition) may be for administration 12 to 16, e.g. 13 to 15, e.g.

14 days after administration of (e.g. after initiation of administration of, e.g. after initiation of daily administration of) a GnRH agonist (e.g. Synarel, Lupron, Decapeptyl). The composition (e.g. pharmaceutical composition) may be for administration with a GnRH agonist. The composition (e.g. pharmaceutical composition) may be for administration prior to administration of a GnRH antagonist (e.g. ganirelix, cetrorelix), for example for administration five or six days prior to administration of a GnRH antagonist. The composition (e.g. pharmaceutical composition) may be for administration with a GnRH antagonist. The composition (e.g. pharmaceutical composition) may be for administration with a GnRH antagonist (e.g. ganirelix, cetrorelix) administered (e.g. daily) from day six of treatment. Preferably the composition (e.g. pharmaceutical composition) is for administration prior to administration of a high (ovulatory) dose of hCG (for example 4,000 to 11,000 IU hCG, e.g. 5,000 IU hCG, 10,000 IU hCG etc.; or 150 to 350 microgram recombinant hCG, for example 250 microgram recombinant hCG) to induce final follicular maturation.

It will be appreciated that the composition may be for dosing at frequencies more (or less) than daily, in which case the relevant doses will be equivalent to the (daily) doses specified herein.

Herein the term "treatment of infertility" includes treatment of infertility by controlled ovarian stimulation (COS) or methods which include a step or stage of controlled ovarian stimulation (COS), for example Intra Uterine Insemination (IUI), in vitro fertilisation (IVF), or intracytoplasmic sperm injection (ICSI). The term "treatment of infertility" includes treatment of infertility by ovulation induction (OI) or by methods which include a step or stage of ovulation induction (OI). The term "treatment of infertility" includes treatment of infertility in a subject having tubal or unexplained infertility, including treatment of infertility in a subject having endometriosis, for example stage I or stage II endometriosis, and/or in a subject having anovulatory infertility, for example WHO type II anovulatory infertility, and/or in a subject with a partner with male factor infertility. The composition may be for (use in) the treatment of infertility (and/or for controlled ovarian stimulation) in a subject having endometriosis, for example in a subject having stage I or stage II endometriosis, as defined by The American Society for Reproductive Medicine (ASRM) classification system for the various stages of endometriosis, (stage IV most severe; stage I least severe) [American Society for Reproductive Medicine. Revised American Society for Reproductive Medicine classification of endometriosis: 1996. Fertil Steril 1997; 67,817 821.].

The composition may be for (use in) the treatment of infertility (and/or for controlled ovarian stimulation) in a subject having normal serum FSH level of 1 to 16 IU/L, for example 1 to 12 IU/L, in the early follicular phase.

The composition may be for (use in) the treatment of infertility (and/or for controlled ovarian stimulation) in a subject identified as being aged 18 to 42 years, for example 25 to 37 years. The product may be for (use in) the treatment of infertility (and/or for controlled ovarian stimulation) in a subject identified as having BMI >15 and BMI <38 kg/m$^2$, for example a subject identified as having BMI >18 and BMI <25 kg/m$^2$, for example a subject having BMI >20 and BMI <25 kg/m$^2$.

The rFSH may have a sialic acid content [expressed in terms of a ratio of moles of sialic acid to moles of protein] of 6 mol/mol or greater, for example between 6 mol/mol and 15 mol/mol, e.g between 8 mol/mol and 14 mol/mol, e.g between 9 mol/mol and 14 mol/mol, for example between 10 mol/mol and 14 mol/mol, e.g between 11 mol/mol and 14 mol/mol, e.g between 12 mol/mol and 14 mol/mol, e.g. between 12 mol/mol and 13 mol/mol. The rFSH may be produced or expressed in a human cell line.

The FSH (rFSH) for use according to the invention may have 1% to 99% of the total sialylation being α2,3-sialylation. The rFSH may have 10% or more of the total sialylation being α2,3-sialylation. For example, 20, 30, 40, 50, 60, 70, 80 or 90% or more of the total sialylation may be α2,3-sialylation. The rFSH may preferably include α2,3-sialylation in an amount which is from 50 to 95% of the total sialylation, for example from 50 to 70% of the total sialylation, for example from 60 to 69% of the total sialylation, for example from 63 to 67%, for example around 65% of the total sialylation. The FSH (rFSH) for use according to the invention may have 1% to 99% of the total sialylation being α2,6-sialylation. The rFSH (or rFSH preparation) of the invention may have 5% or more, for example 5% to 99%, for example 5% to 50%, of the total sialylation being α2,6-sialylation. The rFSH may have 50% or less of the total sialylation being α2,6-sialylation. The rFSH may preferably include α2,6-sialylation in an amount which is from 5 to 50% of the total sialylation, for example from 10 to 50% of the total sialylation, for example from 31 to 38%, for example around 35% of the total sialylation. By sialylation it is meant the amount of sialic residues present on the FSH carbohydrate structures. α2,3-sialylation means sialylation at the 2,3 position (as is well known in the art) and α2,6 sialylation at the 2,6 position (also well known in the art). Thus "% of the total sialylation may be a 2,3 sialylation" refers to the % of the total number of sialic acid residues present in the FSH which are sialylated in the 2,3 position. The term "% of the total sialylation being α2,6-sialylation" refers to the % of the total number of sialic acid residues present in the FSH which are sialylated in the 2,6 position.

The rFSH may have a sialic acid content (amount of sialylation per FSH molecule) of (based on the mass of protein, rather than the mass of protein plus carbohydrate) of 6% or greater (e.g. between 6% and 15%, e.g. between 7% and 13%, e.g. between 8% and 12%, e.g. between 11% and 15%, e.g. between 12% and 14%) by mass.

The rFSH may be produced or expressed in a human cell line, for example a Per.C6 cell line, a HT1080 cell line etc. This may simplify (and render more efficient) the production method because manipulation and control of e.g. the cell growth medium to retain sialylation may be less critical than with known processes. The method may also be more efficient because there is little basic rFSH produced compared to production of known rFSH products; more acidic rFSH is produced and separation/removal of basic FSH is less problematic. The rFSH may be produced or expressed in a PER.C6® cell line, a PER.C6® derived cell line or a modified PER.C6® cell line. rFSH which is produced or expressed in a human cell line (e.g. PER.C6® cell line, HT1080 cell line etc.) will include some α2,6-linked sialic acids (α2,6 sialylation) provided by endogenous sialyl transferase activity [of the cell line] and will include some α2,3-linked sialic acids (α2,3 sialylation) provided by endogenous sialyl transferase activity. The cell line may be modified using α2,3-sialyltransferase. The cell line may be modified using α2,6-sialyltransferase. Alternatively or additionally, the rFSH may include α2,6-linked sialic acids (α2,6 sialylation) provided by endogenous sialyl transferase activity [of the cell line]. Herein, the term "human derived recombinant FSH" means recombinant FSH which is produced or expressed in a human cell line (e.g. recombinant FSH made by engineering a human cell line).

The rFSH may be produced using α2,3- and/or α2,6-sialyltransferase. In an example, rFSH is produced using α2,3-sialyltransferase. The rFSH may include α2,6-linked sialic acids (α2,6 sialylation) provided by endogenous sialyl transferase activity.

The composition may be a pharmaceutical composition. The pharmaceutical composition is for the treatment of infertility. The treatment of infertility may comprise assisted reproductive technologies (ART), ovulation induction or intrauterine insemination (IUD. The pharmaceutical composition may be used, for example, in medical indications where known FSH preparations are used.

The product or composition can be formulated into well-known compositions for any route of drug administration, e.g. oral, rectal, parenteral, transdermal (e.g. patch technology), intravenous, intramuscular, subcutaneous, intrasusternal, intravaginal, intraperitoneal, local (powders, ointments or drops) or as a buccal or nasal spray. A typical composition comprises a pharmaceutically acceptable carrier, such as aqueous solution, non toxic excipients, including salts and preservatives, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others.

Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. The compositions of the present invention also can contain additives such as but not limited to preservatives, wetting agents, emulsifying agents, surfactants and dispersing agents. Antibacterial and antifungal agents can be included to prevent growth of microbes and includes, for example, m-cresol, benzyl alcohol, paraben, chlorobutanol, phenol, sorbic acid, and the like. If a preservative is included, benzyl alcohol, phenol and/or m-cresol are preferred; however, the preservative is by no means limited to these examples. Furthermore, it may be desirable to include isotonic agents such as sugars, sodium chloride, and the like. The product or composition may further comprise a salt comprising a pharmaceutically acceptable alkali metal cation selected from the group consisting of $Na^+$— or $K^+$— salts, or a combination thereof. Preferably the salt is a Na+- salt, for example NaCl or $Na_2SO_4$.

Preferably the product or composition comprises recombinant FSH and one or more of Polysorbate 20, L-methionine, phenol, disodium sulphate and sodium phosphate buffer.

In some cases, to effect prolonged action it is desirable to slow the absorption of FSH (and other active ingredients, if present) from subcutaneous or intramuscular injection. This can be accomplished by the use of a liquid suspension of crystalline or amorphous material with poor water solubility. The rate of absorption of FSH then depends upon its rate of dissolution which, in turn, can depend upon crystal size and crystalline form. Alternatively, delayed absorption of a parenterally administered FSH combination form is accomplished by dissolving or suspending the FSH combination in an oil vehicle. Injectable depot forms can be made by forming microencapsule matrices of the FSH (and other agents, if present) in biodegradable polymers such as polylactide-polyglycolide. Depending upon the ratio of FSH to polymer and the nature of the particular polymer employed, the rate of FSH release can be controlled. Examples of other biodegradable polymers include polyvinylpyrrolidone, poly(orthoesters), poly(anhydrides) etc. Depot injectable formulations are also prepared by entrapping the FSH in liposomes or microemulsions which are compatible with body tissues.

Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like.

The product or composition may be formulated for single use or for multiple use (multiple dose). If the product or composition is formulated for multiple use, it is preferred that a preservative is included. If a preservative is included, benzyl alcohol, phenol and/or m-cresol are preferred; however, the preservative is by no means limited to these examples. The single use or multiple use formulated product or composition may further comprise a salt comprising a pharmaceutically acceptable alkali metal cation selected from the group consisting of $Na^+$— or $K^+$— salts, or a combination thereof. Preferably the salt is a Na+- salt, for example NaCl or $Na_2SO_4$.

The product or composition may be included in a container such as a vial, prefilled cartridge (e.g. for single administration or multiple use) or an injection device such as a "pen" for e.g. administration of multiple doses.

The product or composition may be a formulation (e.g. injectable formulation) including FSH (optionally with hCG, LH, LH activity etc.) The LH activity, if present, may originate from LH or human chorionic gonadotropin, hCG. If there is more than one active ingredient (i.e. FSH and e.g. hCG or LH) these may be suitable for administration separately or together. If administered separately, administration can be sequential. The product can be supplied in any appropriate package. For example, a product can include a number of containers (e.g. pre-filled syringes or vials) containing either FSH or hCG, or a combination (or combination) of both FSH and hCG. The hCG may be recombinant hCG or urinary hCG. If the product includes a number of containers (e.g. pre-filled syringes or vials) containing FSH, e.g. recombinant FSH, each container may include the same amount of FSH. One or more containers may include different amounts of FSH. The syringes or vials may be packaged in a blister package or other means to maintain sterility. Any product can optionally contain instructions for using the FSH (and e.g. hCG if present) formulations. The pH and exact concentration of the various components of the pharmaceutical composition are adjusted in accordance with routine practice in this field. See GOODMAN and GILMAN's THE PHARMACOLOGICAL BASIS FOR THERAPEUTICES, $7^{th}$ ed. In a preferred embodiment, the compositions of the invention are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral compositions can be supplied in liquid formulation or as a solid which will be mixed with a sterile injectable medium just prior to administration. In an especially preferred embodiment, the parenteral compositions are supplied in dosage unit form for ease of administration and uniformity of dosage.

According to the present invention in a further aspect there is provided a method of treatment of infertility [e.g. infertility in a patient having a serum AMH level <15 pmol/L (e.g. 0.05 pmol/L to 14.9 pmol/L) and having variant Ser/Ser at position 680 of the FSH receptor] wherein the treatment of infertility comprises (a) identifying (e.g. determining) the serum AMH level of the patient.

(b) identifying the variant at position 680 of the FSH receptor of the patient; and (c) administering a dose of or equivalent to 9 to 24 µg recombinant follicle stimulating hormone (FSH) per day to a patient (identified as) having a serum AMH level <15 pmol/L (e.g. 0.05 pmol/L to 14.9 pmol/L) and variant Ser/Ser at position 680 of the FSH receptor. The composition may comprise 9 to 24 µg FSH, for example 10 to 18 µg FSH, for example 12 to 16 µg FSH, for example 12 to 15 µg FSH. The composition may comprise >12 µg FSH, for example 12.3 to 24 µg FSH, for example 12.33 to 24 µg FSH, for example 12.67 to 24 µg FSH, for example 13 to 24 µg FSH, for example 13 to 16 µg FSH, for example 13 to 15 µg FSH.

The administration of FSH may be starting on day one of treatment and continuing for six to sixteen days, for example seven to sixteen days, for example 8 to 16 days, for example 8 to 13 days.

The FSH may be recombinant FSH. The FSH may be recombinant FSH including α2,3- and α2,6-sialylation. The FSH may be recombinant FSH including α2,3- and α2,6-sialylation wherein 1 to 99% of the total sialylation is α2,6-sialylation and 99% to 1% of the total sialylation is α2,3-sialylation. The FSH may be recombinant FSH including α2,3- and α2,6-sialylation wherein 1 to 50% of the total sialylation is α2,6-sialylation and 50% to 99% of the total sialylation is α2,3-sialylation. The FSH may be recombinant FSH including α2,3- and α2,6-sialylation wherein 5 to 40% of the total sialylation is α2,6-sialylation and 60% to 95% of the total sialylation is α2,3-sialylation. Preferably the FSH is a human cell line derived recombinant FSH.

The administration preferably comprises a daily dose of, or a daily dose equivalent to, the amount of FSH defined above and in the claims. The (daily) dose may be an initial dose (it may be reduced, increased, or maintained during the treatment).

The method may be a method of treatment of infertility in the patient's (subject's) first stimulation protocol. It will be appreciated that for further stimulation cycles, the doses may be adjusted according to actual ovarian response in the first cycle.

According to the present invention in a further aspect there is provided a composition (e.g. a pharmaceutical composition) comprising FSH for use in the manufacture of a medicament for the treatment of infertility, the composition comprising 9 to 24 µg follicle stimulating hormone (FSH), wherein the medicament is for (e.g. daily) administration to a patient identified as (e.g. selected as) having variant Ser/Ser at position 680 of the FSH receptor (prior to treatment). The medicament may be for (e.g. daily) administration to a patient identified as (e.g. selected as) having variant Ser/Ser at position 680 of the FSH receptor and identified as (e.g. selected as) having a serum AMH level <15 pmol/L (e.g. 0.05 pmol/L to 14.9 pmol/L) (prior to treatment). The composition may comprise 9 to 24 µg FSH, for example 10 to 18 µg FSH, for example 12 to 16 µg FSH, for example 12 to 15 µg FSH. The composition may comprise >12 µg FSH, for example 12.3 to 24 µg FSH, for example 12.33 to 24 µg FSH, for example 12.67 to 24 µg FSH, for example 13 to 24 µg FSH, for example 13 to 16 µg FSH, for example 13 to 15 µg FSH.

The present applicants also found that administration of FSH to patients identified as having low AMH [AMH level <15 pmol/L (e.g. 0.05 pmol/L to 14.9 pmol/L), who would generally be associated with a low response], as well as having variant Asn/Asn or variant Asn/Ser at position 680 of the FSH receptor, provides a good response in terms of follicular development. This is achieved with a reduced dosage of FSH and/or reduced duration of treatment, compared with treatment of patients with low AMH and variant Ser/Ser at position 680 of the FSH receptor. This allows tailoring of the dose of FSH in specific patients identified as having specific AMH level, as well as these specific polymorphisms at the FSHR. As set out below, the expected duration of stimulation for a patient having AMH level <15 pmol/L and variant Asn/Asn is 1.5 days less than the duration of stimulation required for a patient having AMH level <15 pmol/L and variant Ser/Ser (see FIG. 7). Accordingly, tailoring the dose to patients identified, prior to treatment, as having both AMH level <15 pmol/L and variant Asn/Asn (or both AMH level <15 pmol/L and variant Asn/Ser) may allow considerable saving in terms of pharmaceutical cost, as well as reduction in risk of potential side effects due to administration of a higher total dose of FSH than is required in these patients.

According to the present invention in a further aspect there is provided a composition (e.g. a pharmaceutical composition) for use in the treatment of infertility, the composition comprising 10 to 12 µg follicle stimulating hormone (FSH), wherein the composition is for (e.g. daily) administration to a patient identified as (e.g. selected as) having variant Asn/Asn or variant Asn/Ser at position 680 of the FSH receptor (prior to treatment). The composition may be for (e.g. daily) administration to a patient identified as (e.g. selected as) having variant Asn/Asn or variant Asn/Ser at position 680 of the FSH receptor and identified as (e.g. selected as) having a serum AMH level <15 pmol/L (e.g. 0.05 pmol/L to 14.9 pmol/L) (prior to treatment). The composition may be for administration to a patient identified as (e.g. selected as) having variant Asn/Asn at position 680 of the FSH receptor and identified as (e.g. selected as) having a serum AMH level <15 pmol/L (e.g. 0.05 pmol/L to 14.9 pmol/L) (prior to treatment). The composition may comprise 10 to <12 µg FSH, for example 10 to 11.9 µg FSH, for example 11 to 11.9 µg FSH, for example 11.33 or 11.67 µg FSH.

The composition (e.g. pharmaceutical composition) may comprise a daily dose of, or a daily dose equivalent to, the amounts of human derived rFSH defined above, herein, and in the claims. The composition (e.g. pharmaceutical composition) may be for (daily) administration of FSH starting on day one of treatment and continuing for six to sixteen days, for example seven to sixteen days, for example 8 to 16 days, for example 8 to 13 days. The treatment of infertility may comprise a step of identifying (e.g. determining, e.g. measuring) the variant at position 680 of the FSH receptor of the patient; and a step of administering the dose to a patient (identified as) having variant Asn/Asn or variant Asn/Ser at position 680 of the FSH receptor. The treatment of infertility may comprise a step of identifying (e.g. determining, e.g. measuring) the serum AMH level of the patient, and administering the dose to a patient (identified as) having serum AMH level of <15 pmol/L (e.g. 0.05 pmol/L to 14.9 pmol/L).

According to the present invention in a further aspect there is provided a composition (e.g. a pharmaceutical composition) comprising follicle stimulating hormone (FSH) for use in the treatment of infertility in a patient having a serum AMH level <15 pmol/L (e.g. 0.05 pmol/L to 14.9 pmol/L) and having variant Asn/Asn or variant Asn/Ser at position 680 of the FSH receptor, wherein the composition is to be administered at a dose of or equivalent to 10 to 12

µg recombinant FSH per day; and wherein the treatment of infertility comprises a step of identifying (e.g. determining) the serum AMH level of the patient; a step of identifying the variant at position 680 of the FSH receptor of the patient; and a step of administering the composition to a patient (identified as) having a serum AMH level <15 pmol/L (e.g. 0.05 pmol/L to 14.9 pmol/L) and variant Asn/Asn or variant Asn/Ser at position 680 of the FSH receptor. The composition may comprise 10 to <12 µg FSH, for example 10 to 11.9 µg FSH, for example 11 to 11.9 µg FSH, for example 11.33 or 11.67 µg FSH.

The composition (e.g. a pharmaceutical composition) may be for use in the treatment of infertility in a patient having a serum AMH level <15 pmol/L (e.g. 0.05 pmol/L to 14.9 pmol/L) and having variant Asn/Asn at position 680 of the FSH receptor [wherein the treatment of infertility comprises a step of identifying (e.g. determining) the serum AMH level of the patient; a step of identifying the variant at position 680 of the FSH receptor of the patient; and a step of administering the dose to a patient (identified as) having a serum AMH level <15 pmol/L (e.g. 0.05 pmol/L to 14.9 pmol/L) and variant Asn/Asn at position 680 of the FSH receptor].

According to the present invention in a further aspect there is provided a method of treatment of infertility [e.g. infertility in a patient having a serum AMH level <15 pmol/L (e.g. 0.05 pmol/L to 14.9 pmol/L) and having variant Asn/Asn or variant Asn/Ser at position 680 of the FSH receptor] wherein the treatment of infertility comprises (a) identifying (e.g. determining) the serum AMH level of the patient; (b) identifying the variant at position 680 of the FSH receptor of the patient; and (c) administering a dose of or equivalent to 10 to 12 µg recombinant follicle stimulating hormone (FSH) per day to a patient (identified as) having a serum AMH level <15 pmol/L (e.g. 0.05 pmol/L to 14.9 pmol/L) and variant Asn/Asn or variant Asn/Ser at position 680 of the FSH receptor. The composition may comprise 10 to <12 µg FSH, for example 10 to 11.9 µg FSH, for example 11 to 11.9 µg FSH, for example 11.33 or 11.67 µg FSH.

The administration of FSH may be starting on day one of treatment and continuing for six to thirteen days, for example seven to thirteen days, for example 8 to 13 days, for example 8 to 11 days.

According to the present invention in a further aspect there is provided a composition (e.g. a pharmaceutical composition) comprising FSH for use in the manufacture of a medicament for the treatment of infertility, the composition comprising 10 to 12 µg follicle stimulating hormone (FSH), wherein the medicament is for (e.g. daily) administration to a patient identified as (e.g. selected as) having variant Asn/Asn or variant Asn/Ser at position 680 of the FSH receptor (prior to treatment). The medicament may be for (e.g. daily) administration to a patient identified as (e.g. selected as) having variant Asn/Asn or variant Asn/Ser at position 680 of the FSH receptor and identified as (e.g. selected as) having a serum AMH level <15 pmol/L (e.g. 0.05 pmol/L to 14.9 pmol/L) (prior to treatment). The medicament may be for administration to a patient identified as (e.g. selected as) having variant Asn/Asn at position 680 of the FSH receptor and identified as (e.g. selected as) having a serum AMH level <15 pmol/L (e.g. 0.05 pmol/L to 14.9 pmol/L) (prior to treatment). The composition may comprise 10 to <12 µg FSH, for example 10 to 11.9 µg FSH, for example 11 to 11.9 µg FSH, for example 11.33 or 11.67 µg FSH.

It will be appreciated that the FSH, identification of patient's serum AMH level and variant at position 680 of the FSH receptor, etc. for these aspects of the invention may be as for the other aspects of the invention recited herein.

DETAILED DESCRIPTION OF THE INVENTION

The present invention will now be described in more detail with reference to the attached drawings in which:

FIG. 1 shows a plasmid map of the pFSHalpha/beta expression vector;

FIG. 2 shows the α2,3-sialyltransferase (ST3GAL4) expression vector;

FIG. 3 shows the α2,6-sialyltransferase (ST6GAL1) expression vector;

Figures 4, 5:
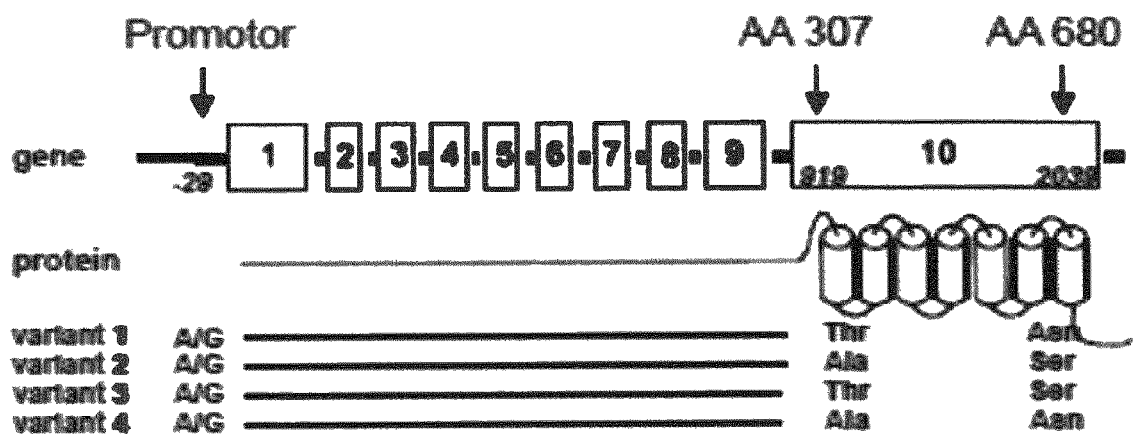

FIG. 4 is a schematic diagram of the FSH Receptor, indicating the position of polymorphisms at amino acid positions 307 and 680 of exon 10, and position 29 in the promoter;

FIG. 5 shows the distribution of SNP Haplotypes at the FSH receptor gene for the 222 patients treated with FSH in the study of Example 8;

FIG. 6 is a table of results showing, for the full analysis set, the observed duration of gonadotropin (FSH) treatment (days) and total gonadotropin (FSH) dose delivered (µg) to patients/subjects having AMH <15 pmol/L in each of the three distinct FSH receptor genotypes with regard to position 680: Asn/Asn, Asn/Ser and Ser/Ser; and FIG. 7 is a table of results showing, for the full analysis set, the expected duration of gonadotropin (FSH) treatment (days) delivered to patients/subjects having AMH <15 pmol/L in each of the three distinct FSH receptor genotypes with regard to position 680: Asn/Asn, Asn/Ser and Ser/Ser, adjusted for dose.

SEQUENCE SELECTION

Human FSH

The coding region of the gene for the FSH alpha polypeptide was used to according to Fiddes and Goodman. (1981). The sequence is banked as AH007338 and at the time of construction there were no other variants of this protein sequence. The sequence is referred herein as SEQ ID NO:1.

The coding region of the gene for FSH beta polypeptide was used according to Keene et al (1989). The sequence is banked as NM_000510 and at the time of construction there were no other variants of this protein sequence. The sequence is referred herein as SEQ ID NO: 2

Sialyltransferase

α2,3-Sialyltransferase—The coding region of the gene for beta-galactoside alpha-2,3-sialyltransferase 4 (α2,3-sialyltransferase, ST3GAL4) was used according to Kitagawa and Paulson (1994). The sequence is banked as L23767 and referred herein as SEQ ID NO: 3.

α2,6-Sialyltransferase—The coding region of the gene for beta-galactosamide alpha-2,6-sialyltransferase 1 (α2,6-sialyltransferase, ST6GAL1) was used according to Grundmann et al. (1990). The sequence is banked as NM_003032 and referred herein as SEQ ID NO: 4.

EXAMPLES

Example 1 Construction of the FSH Expression Vector

The coding sequence of FSH alpha polypeptide (AH007338, SEQ ID NO: 1) and FSH beta polypeptide (NM_003032, SEQ ID NO: 2) were amplified by PCR using the primer combinations FSHa-fw and FSHa-rev and FSHb-fw and FSHb-rec respectively.

```
FSHa-fw
                                     (SEQ ID NO: 9)
5'-CCAGGATCCGCCACCATGGATTACTACAGAAAAATATGC-3'

FSHa-rev
                                    (SEQ ID NO: 10)
5'-GGATGGCTAGCTTAAGATTTGTGATAATAAC-3'

FSHb-fw
                                    (SEQ ID NO: 11)
5'-CCAGGCGCGCCACCATGAAGACACTCCAGTTTTTC-3'

FSHb-rev
                                    (SEQ ID NO: 12)
5'-CCGGGTTAACTTATTATTCTTTCATTTCACCAAAGG-3'
```

The resulting amplified FSH beta DNA was digested with the restriction enzymes AscI and HpaI and inserted into the AscI and HpaI sites on the CMV driven mammalian expression vector carrying a neomycin selection marker. Similarly the FSH alpha DNA was digested with BamHI and NheI and inserted into the sites BamHI and NheI on the expression vector already containing the FSH beta polypeptide DNA.

The vector DNA was used to transform the DH5a strain of E. coli. Colonies were picked for amplification. Colonies containing the vector containing both FSH alpha and beta were selected for sequencing and all contained the correct sequences according to SEQ ID NO: 1 and SEQ ID NO: 2. Plasmid pFSH A+B #17 was selected for transfection (FIG. 1).

Example 2 Construction of the ST3 Expression Vector

The coding sequence of beta-galactoside alpha-2,3-sialyltransferase 4 (ST3, L23767, SEQ ID NO: 3) was amplified by PCR using the primer combination 2,3STfw and 2,3STrev.

```
2,3STfw
                                    (SEQ ID NO: 13)
5'-CCAGGATCCGCCACCATGTGTCCTGCAGGCTGGAAGC-3'

2,3STrev
                                    (SEQ ID NO: 14)
5'-TTTTTTTCTTAAGTCAGAAGGACGTGAGGTTCTTG-3'
```

The resulting amplified ST3 DNA was digested with the restriction enzymes BamHI and AflII and inserted into the BamHI and AflII sites on the CMV driven mammalian expression vector carrying a hygromycin resistance marker. The vector was amplified as previously described and sequenced. Clone pST3 #1 (FIG. 2) contained the correct sequence according SEQ ID NO: 3 and was selected for transfection.

Example 3 Construction of the ST6 Expression Vector

The coding sequence of beta-galactosamide alpha-2,6-sialyltransferase 1 (ST6, NM_003032, SEQ ID NO: 4) was amplified by PCR using the primer combination 2,6STfw and 2,6STrev.

```
2,6STfw
                                    (SEQ ID NO: 15)
5'-CCAGGATCCGCCACCATGATTCACACCAACCTGAAG-3'

2,6STrev
                                    (SEQ ID NO: 16)
5'-TTTTTTTCTTAAGTTAGCAGTGAATGGTCCGG-3'
```

The resulting amplified ST6 DNA was digested with the restriction enzymes BamHI and AflII and inserted into the BamHI and AR sites on the CMV driven mammalian expression vector carrying a hygromycin resistance marker. The vector was amplified as previously described and sequenced. Clone pST6 #11 (FIG. 3) contained the correct sequence according SEQ ID NO: 4 and was selected for transfection.

Example 4 Stable Expression of pFSH α+β in PER.C6® Cells. Transfection Isolation and Screening of Clones PER.C6®clones producing FSH were generated by expressing both polypeptide chains of FSH from a single plasmid (see Example 1).

To obtain stable clones a liposome based transfection agent with the pFSH α+β construct. Stable clones were selected in VPRO supplemented with 10% FCS and containing G418. Three weeks after transfection G418 resistant clones grew out. Clones were selected for isolation. The isolated clones were cultured in selection medium until 70-80% confluent. Supernatants were assayed for FSH protein content using an FSH selective ELISA and pharmacological activity at the FSH receptor in cloned cell line, using a cAMP accumulation assay. Clones expressing functional protein were progressed for culture expansion to 24 well, 6 well and T80 flasks.

Studies to determine productivity and quality of the material from seven clones were initiated in T80 flasks to generate sufficient material. Cells were cultured in supplemented media as previously described for 7 days and the supernatant harvested. Productivity was determined using the FSH selective ELISA. The isoelectric profile of the material was determined by Isoelectric focusing (IEF), by methods known in the art. Clones with sufficient productivity and quality were selected for sialyltransferase engineering.

Example 5 Level of Sialylation is Increased in Cells that Over Express α2,3-Sialyltransferase. Stable Expression of pST3 in FSH Expressing PER.C6® Cells; Transfection Isolation and Screening of Clones PER.C6® clones producing highly sialylated FSH were generated by expressing α2,3 sialyltransferase from separate plasmids (Example 2) in PER.C6® cells already expressing both polypeptide chains of FSH (from Example 4). Clones produced from PER.C6® cells as set out in Example 4 were selected for their characteristics including productivity, good growth profile, production of functional protein, and produced FSH which included some sialylation. Stable clones were generated as previously described in Example 4. Clones were isolated, expanded and assayed. The α2,3-sialyltransferase clones were adapted to serum free media and suspension conditions.

As before, clones were assayed using a FSH selective ELISA, functional response in an FSH receptor cell line, IEF, metabolic clearance rate and Steelman Pohley analysis. Results were compared to a commercially available recombinant FSH (Gonal-f, Serono) and the parental FSH PER.C6®cell lines. FSH produced by most of the clones has significantly improved sialylation (i.e. on average more FSH isoforms with high numbers of sialic acids) compared to FSH expressed without α2,3-sialyltransferase. In conclusion expression of FSH together with sialyltransferase in PER.C6® cells resulted in increased levels of sialylated FSH compared to cells expressing FSH only.

Example 6 Production and Purification Overview

A procedure was developed to produce FSH in PER.C6® cells that were cultured in suspension in serum free medium. The procedure is described below and was applied to several FSH-producing PER.C6® cell lines.

FSH from α2,3-clone (Example 5) was prepared using a using a modification of the method described by Lowry et al. (1976).

For the production of PER.C6®-FSH, the cell lines were adapted to a serum-free medium, i.e., Excell 525 (JRH Biosciences). The cells were first cultured to form a 70%-90% confluent monolayer in a T80 culture flask. On passage the cells were re-suspended in the serum free medium, Excell 525+4 mM L-Glutamine, to a cell density of $0.3 \times 10^6$ cells/ml. A 25 ml cell suspension was put in a 250 ml shaker flask and shaken at 100 rpm at 37° C. at 5% $CO_2$. After reaching a cell density of $>1 \times 10^6$ cells/ml, the cells were sub-cultured to a cell density of 0.2 or $0.3 \times 10^6$ cells/ml and further cultured in shaker flasks at 37° C., 5% $CO_2$ and 100 rpm.

For the production of FSH, the cells were transferred to a serum-free production medium, i.e., VPRO (JRH Biosciences), which supports the growth of PER.C6® cells to very high cell densities (usually $>10^7$ cells/ml in a batch culture). The cells were first cultured to $>1 \times 10^6$ cells/ml in Excell 525, then spun down for 5 min at 1000 rpm and subsequently suspended in VPRO medium+6 mM L-glutamine to a density of $1 \times 10^6$ cells/ml. The cells were then cultured in a shaker flask for 7-10 days at 37° C., 5% $CO_2$ and 100 rpm. During this period, the cells grew to a density of $>10^7$ cells/ml. The culture medium was harvested after the cell viability started to decline. The cells were spun down for 5 min at 1000 rpm and the supernatant was used for the quantification and purification of FSH. The concentration of FSH was determined using ELISA (DRG EIA 1288).

Thereafter, purification of FSH was carried out using a modification of the method described by Lowry et al. (1976). Purification using charge selective chromatography was carried out to enrich the highly sialylated forms by methods well known in the art.

During all chromatographic procedures, enrichment of the sialylated forms of FSH as claimed herein was confirmed by RIA (DRG EIA 1288) and/or IEF.

Example 7 Quantification of Relative Amounts of α2,3 and α2,6 Sialic Acid

The relative percentage amounts of α2,3 and α2,6 sialic acid on purified rFSH (Example 6) were measured using known techniques.

N-Glycans were released from the samples using PNGase F under denaturative conditions and then labelled with 2-aminobenzamide. Released glycan forms were then separated and analysed by Weak Anion Exchange (WAX) column for determination of charge distribution. Labelled glycans treated with 2,3,6,8 sialidase for determination of total sialic acid and 2,3 sialidase for determination of 2,3 sialic acid, were further analyzed by wax column.

The relative percentages of the charged glycans were calculated from structures present in the undigested and digested glycan pools and are shown in FIG. 4 (for 8 samples). These were found to be in the ranges 50%-95% (e.g. about 80% to 90%) for α2,3 sialylation and 5% to 50%, generally about 10 to 20% (or about 31% or 35%), for α2,6 sialylation.

Example 8—A Multiple Dose Study Investigating FE 999049 in Comparison to GONAL-F The following describes a randomised, controlled, assessor-blind, parallel groups, multinational, multicentre trial assessing the dose-response relationship of FE 999049 in patients undergoing controlled ovarian stimulation for in vitro fertilisation (IVF)/intracytoplasmic sperm injection (ICSI). The patient population was 265 IVF patients aged between 18 to 37 years, with BMI 18.5 to 32.0 kg/m².

The trial was designed as a dose-response trial with number of oocytes retrieved as the primary endpoint. Secondary endpoints will explore the qualitative and quantitative impact of different doses of FE 999049 with regard to endocrine profile, follicular development, oocyte fertilisation, embryo quality and treatment efficiency (i.e. total gonadotropin consumption and duration of stimulation). The trial is designed to evaluate the efficacy of FE 999049 to establish pregnancy when used in controlled ovarian stimulation for IVF/ICSI cycles.

Subjects were assessed within 3 months prior to randomisation for compliance with the inclusion and exclusion criteria, including an anti-Müllerian hormone (AMH) assessment to increase homogeneity of the trial population in relation to ovarian response and minimise the number of potential poor and hyper-responders to the FE 999049 doses and GONAL-F dose used in the trial. The AMH assessment was measured using the AMH Gen-II enzyme linked immunosorbent assay kit (Beckman Coulter, Inc., Webster, Tex.). This assay can detect AMH concentrations greater than 0.57 pmol/L with a minimum limit of quantitation of 1.1 pmol/L.

On day 2-3 of their menstrual cycle, subjects were randomised in a 1:1:1:1:1:1 fashion to treatment with either 90 IU, 120 IU, 150 IU, 180 IU or 210 IU FE 999049 or 150 IU GONAL-F, and ovarian stimulation initiated. Randomisation was stratified according to AMH level at screening [5.0-14.9 pmol/L (low AMH) and 15.0 to 44.9 pmol/L (high AMH)).

Gonal-F is filled by mass (FbM) at FDA request; referring to μg dose is therefore appropriate. The Gonal-F label indicates 600 IU/44 μg, which indicates that 150 IU is 11 μg. However, there is some variation and the batch certificate for this trial indicated that 11.3 μg Gonal-F was equivalent to 150 IU. The FE999049 doses are presented by protein content (μg) rather than biological activity. Thus the doses of FE999049 were 5.2 μg (90 IU), 6.9 μg (120 IU), 8.6 μg (150 IU), 10.3 μg (180 IU) or 12.1 μg (210 IU).

The subject and dose distribution is set out as follows (data are number of subjects):

TABLE 1

| | FE 999049 | | | | | GONAL-F 11.3 (11) µg | Total |
|---|---|---|---|---|---|---|---|
| | 5.2 µg | 6.9 µg | 8.6 µg | 10.3 µg | 12.1 µg | | |
| Screened | | | | | | | 334 |
| Randomised and exposed | 42 | 45 | 44 | 45 | 46 | 43 | 265 |
| High AMH strata (15.0-44.9 pmol/L) | 23 | 26 | 24 | 24 | 26 | 25 | 148 (56%) |
| Low AMH strata (5.0-14.9 pmol/L) | 19 | 19 | 20 | 20 | 21 | 18 | 117 (44%) |
| Per-protocol | 40 | 42 | 42 | 44 | 44 | 43 | 255 |

The daily dose level of FE 999049 or GONAL-F is fixed throughout the entire stimulation period. During stimulation, subjects are monitored on stimulation day 1, 4 and 6 and hereafter at least every second day. When 3 follicles of ≥15 mm are observed, visits are performed daily. Subjects are treated with FE 999049 or GONAL-F for a maximum of 16 days.

To prevent a premature LH surge, a GnRH antagonist (ganirelix acetate, ORGALUTRAN, MSD/Schering-Plough) may be initiated on stimulation day 6 at a daily dose of 0.25 mg and continued throughout the stimulation period. Triggering of final follicular maturation is done on the day when ≥3 follicles with a diameter ≥17 mm are observed. If there are <25 follicles with a diameter ≥12 mm, 250 µg recombinant hCG (choriogonadotropin alfa, OVITRELLE, Merck Serono/EMD Serono) is administered. If there are 25-35 follicles with a diameter ≥12 mm, 0.2 mg GnRH agonist (triptorelin acetate, DECAPEPTYL/GONAPEPTYL, Ferring Pharmaceuticals) is administered. In case of excessive ovarian response, defined as >35 follicles with a diameter ≥12 mm, the treatment is cancelled. In case of poor ovarian response, defined as <3 follicles with a diameter >10 mm observed on stimulation day 10, the cycle could be cancelled.

Oocyte retrieval takes place 36 h (±2 h) after triggering of final follicular maturation and the oocytes inseminated by IVF and/or ICSI. Fertilisation and embryo development are assessed from oocyte retrieval to the day of transfer. For subjects who underwent triggering of final follicular maturation with hCG, one blastocyst of the best quality available is transferred on day 5 after oocyte retrieval while remaining blastocysts are frozen. For subjects who undergo triggering of final follicular maturation with GnRH agonist, no embryo transfer takes place in the fresh cycle and blastocysts are instead frozen on day 5. Vaginal progesterone tablets (LUTINUS, Ferring Pharmaceuticals) 100 mg 3 times daily are provided for luteal phase support from the day after oocyte retrieval until the day of the clinical pregnancy visit. A βhCG test is performed 13-15 days after embryo transfer and clinical pregnancy will be confirmed by transvaginal ultrasound (TVU) 5-6 weeks after embryo transfer.

Results

The number of oocytes retrieved (primary endpoint) is shown in the following Table.

TABLE 2

| | FE 999049 | | | | | GONAL-F 11.3 (11)µg |
|---|---|---|---|---|---|---|
| | 5.2 µg | 6.9 µg | 8.6 µg | 10.3 µg | 12.1 µg | |
| Oocytes retrieved | | | | | | |
| All | 5.2 (3.3) | 7.9 (5.9) | 9.2 (4.6) | 10.6 (7.0) | 12.2 (5.9) | 10.4 (5.2) |
| High AMH | 5.9 (3.9) | 9.1 (6.4) | 10.6 (4.8) | 13.6 (7.8) | 14.4 (5.8) | 12.4 (5.4) |
| Low AMH | 4.5 (2.2) | 6.3 (4.9) | 7.4 (3.8) | 6.9 (3.6) | 9.4 (4.9) | 7.8 (3.4) |

Data are mean (SD)

The primary objective was met: a significant dose-response relationship was established for FE 999049 with respect to number of oocytes retrieved. This finding was observed not only for the overall trial population, but also for each of the two AMH strata used at randomisation.

A significant dose-response for FE 999049 was demonstrated for all key objective pharmacodynamic parameters, e.g. estradiol, inhibin B and inhibin A. At a similar microgram dose level, the pharmacodynamic responses with FE 999049 were larger than with GONAL-F (these results not shown).

The serum FSH concentrations after exposure to FE 999049 were significantly higher than for GONAL-F. The results confirm that the PK profile of FE 999049 differs from that of GONAL-F. Fertilisation rates, blastocyst development and pregnancy rates in IVF/ICSI patients treated with FE 999049 were within expectations.

There were no safety concerns with the use of FE 999049. A good local tolerability was documented.

Further Analysis

The applicants have further analysed the data to identify the FE 999049 dose(s) that fulfil the following criteria with respect to number of oocytes retrieved:

Oocytes retrieved in the range 8-14

Minimise proportion of patients with <8 oocytes

Minimise proportion of patients with <4 or ≥20 oocytes

Low AMH Strata

As seen in Table 2, the dose of FE999049 which fulfilled the first criterion (Oocytes retrieved in the range 8-14) was 12.1 µg (mean 9.4 oocytes retrieved). The distribution of oocytes is shown in Table 3 below.

TABLE 3

| Oocytes retrieved | FE 999049 | | | | | GONAL-F 11.3 (11)µg |
|---|---|---|---|---|---|---|
| | 5.2 µg | 6.9 µg | 8.6 µg | 10.3 µg | 12.1 µg | |
| <4 | 32% | 24% | 15% | 10% | 10% | 6% |
| 4-7 | 63% | 42% | 45% | 60% | 20% | 56% |
| 8-14 | 5% | 24% | 35% | 30% | 60% ↔ | 33% |
| 15-19 | 0% | 5% | 5% | 0% | 5% | 6% |
| ≥20 | 0% | 5% | 0% | 0% | 5% | 0% |

Data are % of subjects

As shown by the arrow, a dose of 12.1 µg FE999049 provides retrieval of the most desirable number of oocytes in 60% of subjects in the low AMH group. This is a marked improvement on Gonal-F (most desirable number of oocytes in only 33% of subjects). There were no indications of early OHSS of a moderate or severe nature and there were no incidences of preventative action being required; there are no concerns associated with the dose of 12.1 µg FE999049 in a patient having low AMH.

Thus the applicants have found that a dose of, or dose equivalent to, 6 to 24 μg, for example 9 to 14 μg, for example 12 μg, human derived recombinant FSH is suitable for use in the treatment of infertility in a patient having serum AMH <15 pmol/L, for example 0.05-14.9 pmol/L for example 5.0-14.9 pmol/L. The dose provides an effective response while minimising risk of OHSS.

Exploratory Evaluation

As an exploratory evaluation, the present inventors investigated the contribution of FSH receptor polymorphism on ovarian response and treatment efficiency following stimulation with FE999049.

Genomic DNA from all patients in the trial was analysed for single nucleotide polymorphism (SNP) at positions 29, 307 and 680 of the FSH-R at the University of Modena and Reggio Emilia, Italy. FIG. 4 is a schematic diagram of the FSH Receptor, indicating the position of polymorphisms at amino acid positions 307 and 680 of exon 10, and position 29 in the promoter. This distribution of SNP FSH-R combinations is as follows: AA 7%, AG 35% and GG 58% for position 29; Thr/Thr 29%, Ala/Thr 54% and Ala/Ala 17% for position 307; and Asn/Asn 30%, Asn/Ser 53% and Ser/Ser 17% for position 680. FIG. 5 shows the distribution of SNP Haplotypes at the FSH receptor gene for the 222 patients treated with FSH in the study of Example 8. The distribution for each position and the overall combinations was not significantly different between the low AMH and high AMH strata.

The results of the clinical trial were further analysed to assess whether SNP had any effect on the duration of treatment and total dose required. This was done for the low AMH group and the high AMH group.

FSHR polymorphism was examined by PCR (Polymerase Chain Reaction) and RFLP (Restriction fragment length polymorphism) by methods known in the art. Women were classified as Asn/Asn, Asn/Ser, and Ser/Ser genotypes. The genetic analysis was described in the following overview protocol and the patients signed a special informed consent. The samples were taken as part of the other blood samples on stimulation day 1. They were measured at the University of Modena and Reggio Emilia.

Overview of Procedures Used for SNP-Analysis at the FSH Receptor Gene

General Procedures:
 1. Genomic DNA extraction (from blood using Nucleon Genomic DNA extraction kit, GE HEALTHCARE)
 2. Operating procedures using nanodrop.

Hrm Procedures:
SNPs genotyping by high resolution melting (HRM) methodology (using SsoFast EvaGreen Supermix cod enzyme. 172-5201, Bio-Rad; HSP-96 plates, cat. HSP9645, Bio-Rad; and CFX96 real-time thermal cycler Bio-Rad.)

Sequencing Procedures

In case of doubt about HRM results, (after two independent HRM on the same samples), the following sequencing procedures are utilised:
 1. PCR reaction and amplification.
 2. PCR product purification.
 3. Quantification of purified PCR.
 4. Sequence reaction protocol.
 5. Sequence product purification.
 6. Capillary electrophoresis run by ABI PRISM 3130 instrument.
 7. Assessment and validation of the results obtained by capillary electrophoresis sequencing with ABI PRISM 3100.

Results

FIG. 7 is a table of results showing, for the full analysis set, the expected duration of gonadotropin (FSH) treatment (days) delivered to patients/subjects having AMH <15 pmol/L in each of the three distinct FSH receptor genotypes with regard to position 680: Asn/Asn, Asn/Ser and Ser/Ser, adjusted for dose.

FIG. 7 shows that the expected mean duration of treatment required for stimulation of a patient having AMH level <15 pmol/L and variant Ser/ser is 9.59 days, which is about 1.5 days longer than that required for stimulation of a patient having AMH level <15 pmol/L and variant Asn/Asn (8.13 days), and about 1.3 days longer than that required for stimulation of a patient having AMH level <15 pmol/L and variant Ser/Asn (8.26 days).

As indicated above, success (in terms of pregnancy and/or live birth) is more likely if the patient has an adequate response (expected ovarian multifollicular development, rise in circulating 17-β-estradiol) occurring within an ideal treatment window. Success is further enhanced if the response is within the centre of this treatment window; that is, not too early in the window and not too late. Reduction of the duration of treatment in patients having low AMH and variant Ser/Ser at position 680 of the FSH receptor (by increasing the dose above 12 μg) may bring the response towards the centre of the treatment window, with enhanced likelihood of success.

Accordingly, tailoring the dose to patients identified as having AMH level <15 pmol/L and variant Ser/Ser prior to treatment may be possible. Identification of patients having Ser/Ser prior to treatment may allow the starting dose to be increased in these patients, compared with those having Ser/Asn and Asn/Asn.

As set out above, a dose of 12.1 μg FE999049 provides retrieval of the most desirable number of oocytes in 60% of subjects in the low AMH group (Table 3). The low AMH group shown in Table 3 included patients having variant Ser/Ser, as well as those having Ser/Asn and Asn/Asn. Administration of a higher starting dose (for example 9 to 24 μg, for example >12 to 24 μg, e.g. 12.33 μg or 13 μg human derived recombinant) of FSH to patients having low AMH [AMH level <15 pmol/L, (e.g. 0.05 pmol/L to 14.9 pmol/L, e.g. 5.0 pmol/L to 14.9 pmol/L)], as well as having variant Ser/Ser at position 680 of the FSH receptor, may be advantageous because it may provide increased probability of success (in terms of pregnancy and/or live birth) and better predictability of success.

FIG. 7 shows that the mean duration of treatment required for stimulation of a patient having AMH level <15 pmol/L and variant Asn/Asn is 8.13 days, and that required for stimulation of a patient having AMH level <15 pmol/L and variant Ser/Asn is 8.26 days, about 1.5 to 1.3 days shorter than the duration for equivalent treatment of a patient having AMH level <15 pmol/L and variant Ser/Ser (9.59 days). Thus, identification of patients having AMH level <15 pmol/L and variant Ser/Asn and Asn/Asn prior to treatment may allow the starting dose for these patients to be reduced to less than 12 μg FE 999049, e.g. 10 to 12 μg, or the duration of treatment to be reduced, while still providing a good response in terms of follicular development. This may provide a benefit in terms of cost of the pharmaceutical, and also in terms of reduction in risk associated with administration of a higher dose than is required for effect in these patients.

FIG. 6 is a table of results showing, for the full analysis set, the observed duration of gonadotropin (FSH) treatment (days) and total gonadotropin (FSH) dose delivered (μg) to patients/subjects having AMH <15 pmol/L in each of the three distinct FSH receptor genotypes with regard to position 680: Asn/Asn, Asn/Ser and Ser/Ser. This confirms the effects shown in FIG. 7.

The results did not show this effect related to SNP in the high AMH population.

This allows tailoring of the dose of FSH in specific patients identified as having specific AMH level, and specific polymorphism at the FSHR.

Example 9—Individualised COS Protocol (Low AMH)

The selected patients are about to undergo COS for in vitro fertilisation (IVF)/intracytoplasmic sperm injection (ICSI) by methods known in the art. The pre-treatment protocol includes assessment/screening of the patient's serum AMH using the AMH Gen-II enzyme linked immunosorbent assay kit (Beckman Coulter, Inc., Webster, Tex.). This assay can detect AMH concentrations greater than 0.57 pmol/L with a minimum limit of quantitation of 1.1 pmol/L. AMH may be measured using other Assay kits (e.g. available from Roche). The pre-treatment protocol includes identification of the allelic variant at position 680 of the FSH receptor following extraction of genomic DNA by methods well known in the art (e.g. by means of a kit for extraction of genomic DNA from blood, and subsequent DNA sequencing, as described in e.g. Gromoll et al, Methods, 21, 83-97 (2000), Simoni et al, Journal of Clinical Endocrinology and Metabolism, Vol 84, No. 2, 751-755 (1999), Falconer et al, Acta Obstet Gynecol Scand 2005: 84: 806-811 (2005), and references therein, or by a PCR and RFLP method such as that set out in Loutradis et al, Journal of Assisted Reproduction and Genetics, Vol. 23, No. 4, April 2006).

The COS protocol proceeds in the usual manner apart from administration of the initial dose of FE 999049 according to AMH level at screening. A patient with an AMH level of <15 pmol/L and variant Ser/Asn or Asn/Asn would be administered an initial daily dose of approximately 12 μg FE 999049, a human derived recombinant FSH product manufactured according to the method of Example 6, or <12 μg FE 999049, e.g. 10 to 12 μg, e.g. 11.33 μg or 11.67 μg, of the human derived recombinant FSH. A patient with an AMH level of <15 pmol/L and variant Ser/Ser would receive a higher initial daily dose greater than 12 μg (e.g. 12.33 to 24 μg, or 13-24 μg of the human derived recombinant FSH.

REFERENCES

Andersen C Y, Westergaard L G, and van Wely M. (2004). FSH isoform composition of commercial gonadotrophin preparations: a neglected aspect? Reprod Biomed Online. 9 231-236.

Arey B J, Stevis P E, Deecher D C, Shen E S, Frail D E, Negro-Vilar A, and Lopez F J. (1997) Induction of promiscuous G protein coupling of the follicle-stimulating hormone (FSH) receptor: a novel mechanism for transducing pleiotropic actions of FSH isoforms. Mol Endocrinol. 11(5), 517-526.

Baenziger J U and Green E D. (1988). Pituitary glycoprotein hormone oligosaccharides: structure, synthesis and function of the asparagine-linked oligosaccharides on lutropin, follitropin and thyrotropin. Biochim Biophys Acta. 947 (2), 287-306.

Bassett R M, and Driebergen R. (2005). Continued improvements in the quality and consistency of follitropin alfa, recombinant human FSH. Reprod Biomed Online. 10(2), 169-177.

Damian-Matsumura P, Zaga V, Maldonado A, Sanchez-Hernandez C, Timossi C, and Ulloa-Aguirre A. (1999). Oestrogens regulate pituitary alpha2,3-sialyltransferase messenger ribonucleic acid levels in the female rat. J Mol Endocrinol. 23(2), 153-165.

D'Antonio M., Borrelli F., Datola A., Bucci R., Mascia M., Polletta P., Piscitelli D., and Papoian R. (1999) Biological characterization of recombinant human follicle stimulating hormone isoforms. Human Reproduction 14, 1160-1167

Dalpathado D S, Irungu J, Go E P, Butnev V Y, Norton K, Bousfield G R, and Desaire H. (2006). Comparative glycomics of the glycoprotein follicle stimulating hormone: glycopeptide analysis of isolates from two mammalian species. Biochemistry. 45(28), 8665-8673.

Dias J A, Van Roey P. (2001). Structural biology of human follitropin and its receptor. Arch Med Res. 32(6), 510-519

Fiddes, J. C. and Goodman, H. M. (1979) Isolation, cloning and sequence analysis of the cDNA for the alpha-subunit of human chorionic gonadotropin. Nature, 281, 351-356.

Flack, M. R., Bennet, A. P., Froehlich, J. Anasti, J N and Nisula, B. (1994). Increased biological activity due to basic isoforms in recombinant human follicle-stimulating hormone produced in a human cell line. J. Clin. Endocrinol. Metab., 79, 756-760

Fox K M, Dias J A, and Van Roey P. (2001). Three-dimensional structure of human follicle-stimulating hormone. Mol Endocrinol. 15(3), 378-89

Grabenhorst E, Hoffmann A, Nimtz M, Zettlmeissl G, and Conradt H S. (1995). Construction of stable BHK-21 cells coexpressing human secretory glycoproteins and human Gal (beta 1-4)GlcNAc-R alpha 2,6-sialyltransferase alpha 2,6-linked NeuAc is preferentially attached to the Gal (beta 1-4)GlcNAc (beta 1-2)Man(alpha 1-3)-branch of diantennary oligosaccharides from secreted recombinant beta-trace protein. Eur J Biochem. 232(3), 718-25.

Green E D and Baenziger J U. (1988). Asparagine-linked oligosaccharides on lutropin, follitropin, and thyrotropin. II. Distributions of sulfated and sialylated oligosaccharides on bovine, ovine, and human pituitary glycoprotein hormones. J Biol Chem. 263(1), 36-44.

Grundmann, U., Nerlich, C., Rein, T. and Zettlmeissl, G. (1990). Complete cDNA sequence encoding human beta-galactoside alpha-2,6-sialyltransferase. G Nucleic Acids Res. 18 (3), 667

Howles, C. M. (1996). Genetic engineering of human FSH (Gonal-F). Hum Reprod. Update, 2, 172-191.

Kagawa Y, Takasaki S, Utsumi J, Hosoi K, Shimizu H, Kochibe N, and Kobata A. (1988). Comparative study of the asparagine-linked sugar chains of natural human interferon-beta 1 and recombinant human interferon-beta 1 produced by three different mammalian cells. J Biol Chem. 263(33), 17508-17515.

Keene, J. L., Matzuk, M. M., Otani, T., Fauser, B, C, J, M., Galway, A. B., Hsueh, A. J. W. and Boime, I. (1989). Expression of Biologically active Human Follitropin in Chinese Hamster Ovary Cells. The Journal of Biological Chemistry 264(9), 4769-4775.

Kitagawa, H. and Paulson, J. C (1994) Cloning of a novel alpha 2,3-sialyltransferase that sialylates glycoprotein and glycolipid carbohydrate groups. J. Biol. Chem. 269(2), 1394-1401.

Lee E U, Roth J, and Paulson J C (1989) Alteration of terminal glycosylation sequences on N-linked oligosaccharides of Chinese hamster ovary cells by expression of beta-galactoside alpha 2,6-sialyltransferase. J Biol Chem. 264(23) 13848-13855.

de Leeuw, R., Mulders, J., Voortman, G. Rombout, F. Damm, J. and Kloosterboer, L. (1996) Structure-function relationship of recombinant follicle stimulating hormone (Puregon). Mol. Hum. Reprod., 2, 361-369.

Lowry O H, Rosebrough N J, Farr A L, Randall R J. (1951) Protein measurement with the Folin phenol reagent. J Biol Chem. 193(1), 265-75.

Lowry, PJ, McLean, C, Jones R L and Satgunasingam N. (1976) Purification of anterior pituitary and hypothalamic hormones Clin Pathol Suppl (Assoc Clin Pathol). 7, 16-21.

Olivennes F, Howles C M, Borini A, Germond M, Trew G, Wikland M, Zegers-Hochschild F, Saunders H (2009) Individualizing FSH dose for assisted reproduction using a novel algorithm: the CONSORT study. Reprod Biomed Online. 2009 February; 18(2):195-204.

Pierce J G, and Parsons T F (1981) Glycoprotein hormones: structure and function Annu Rev Biochem. 50, 465-495.

Pricer W E Jr, and Ashwell G. (1971). The binding of desialylated glycoproteins by plasma membranes of rat liver. J Biol Chem. 246(15), 4825-33.

Rathnam P, and Saxena B B. (1975). Primary amino acid sequence of follicle-stimulating hormone from human pituitary glands. I. alpha subunit. J Biol Chem.; 250(17): 6735-6746.

Regoeczi E, Debanne M T, Hatton M C, and Koj A. (1978) Elimination of asialofetuin and asialoorosomucoid by the intact rat. Quantitative aspects of the hepatic clearance mechanism. Biochim Biophys Acta. 541(3), 372-84.

Royle L, Radcliffe C M, Dwek R A and Rudd P M (2006) Methods in Molecular Biology, ed I Brockhausen-Schutzbach (Humana Press), 347: Glycobiology protocols, 125-144.

Ryan R J, Keutmann H T, Charlesworth M C, McCormick D J, Milius R P, Calvo F O and Vutyavanich T. (1987). Structure-function relationships of gonadotropins. Recent Prog Horm Res.; 43,:383-429.

Saxena B B and Rathnam P. (1976) Amino acid sequence of the beta subunit of follicle-stimulating hormone from human pituitary glands. J Biol Chem. 251(4), 993-1005

Steelman S L, and Pohley F M. (1953) Assay of the follicle stimulating hormone based on the augmentation with human chorionic gonadotropin. Endocrinology. 53(6) 604-616.

Steer C J, and Ashwell G. (1980) Studies on a mammalian hepatic binding protein specific for asialoglycoproteins. Evidence for receptor recycling in isolated rat hepatocytes. J Biol Chem. 255(7), 3008-13.

Svensson E C, Soreghan B, and Paulson J C. (1990) Organization of the beta-galactoside alpha 2,6-sialyltransferase gene. Evidence for the transcriptional regulation of terminal glycosylation. J Biol Chem. 265(34):20863-20868.

Takeuchi M, Takasaki S, Miyazaki H, Kato T, Hoshi S, Kochibe N, and Kobata A (1988). Comparative study of the asparagine-linked sugar chains of human erythropoietins purified from urine and the culture medium of recombinant Chinese hamster ovary cells. J Biol Chem. 263(8), 3657-3663.

Timossi C M, Barrios de Tomasi J, Zambrano E, Gonzalez R, Ulloa-Aguirre A. (1998). A naturally occurring basically charged human follicle-stimulating hormone (FSH) variant inhibits FSH-induced androgen aromatization and tissue-type plasminogen activator enzyme activity in vitro. Neuroendocrinology. 67(3), 153-163.

Timossi C M, Barrios-de-Tomasi J, Gonzalez-Suarez R, Arranz M C, Padmanabhan V, Conn P M, and Ulloa-Aguirre A. (2000). Differential effects of the charge variants of human follicle-stimulating hormone. J Endocrinol. 165(2), 193-205.

Ulloa-Aguirre, A., Espinoza, R., Damian-Matsumura, P. and Chappel, S. C. (1988) Immunological and biological potencies of the different molecular species of gonadotrophins. Hum. Reprod. 3, 491-501.

Ulloa-Aguirre, A., Cravioto, A., Damián-Matsumura, P. Jimenez, M, Zambrano, E and Diaz-Sanchez, V. (1992) Biological characterization of the naturally occurring analogues of intrapituitary human follicle stimulating hormone. Hum. Reprod. 7, 23-30.

Ulloa-Aguirre A, Midgley A R Jr, Beitins I Z, and Padmanabhan V. (1995). Follicle-stimulating isohormones: characterization and physiological relevance. Endocr Rev.16(6), 765-787.

Ulloa-Aguirre A, Maldonado A, Damián-Matsumura P, and Timossi C (2001). Endocrine regulation of gonadotropin glycosylation. Arch Med Res. 32(6), 520-532.

Ulloa-Aguirre A, Timossi C, Barrios-de-Tomasi J, Maldonado A, and Nayudu P. (2003). Impact of carbohydrate heterogeneity in function of follicle-stimulating hormone: studies derived from in vitro and in vivo models. Biol Reprod. 69(2), 379-389.

Van Lenten L, and Ashwell G. (1972) The binding of desialylated glycoproteins by plasma membranes of rat liver. Development of a quantitative inhibition assay. J Biol Chem. 247(14), 4633-40.

Wide, L. and Albertsson-Wikland, K. (1990) Change in electrophoretic mobility of human follicle-stimulating hormone in serum after administration of gonadotropin-releasing hormone. J. Clin. Endocrinol. Metab. 70, 271-276.

Wide, L. and Bakos, 0. (1993). More basic forms of both human follicle-stimulating hormone and luteinizing hormone in serum at midcycle compared with the follicular or luteal phase. J. Clin. Endocrinol. Metab., 76, 885-889.

Wide L, Naessén T, Sundström-Poromaa I, Eriksson K. (2007) Sulfonation and sialylation of gonadotropins in women during the menstrual cycle, after menopause, and with polycystic ovarian syndrome and in men. J Clin Endocrinol Metab.; 92(11), 4410-4417.

Zambrano E, Zariñán T, Olivares A, Barrios-de-Tomasi J, and Ulloa-Aguirre A. (1999). Receptor binding activity and in vitro biological activity of the human FSH charge isoforms as disclosed by heterologous and homologous assay systems: implications for the structure-function relationship of the FSH variants. Endocrine. 10(2), 113-121.

Zhang X, Lok S H, and Kon O L (1998) Stable expression of human alpha-2,6-sialyltransferase in Chinese hamster ovary cells: functional consequences for human erythropoietin expression and bioactivity. Biochim Biophys Acta. 1425(3), 441-452.

FIGS. 1, 2 and 3: Plasmid maps of the pFSHalpha/beta, pST3 and pST6 expression vectors. CMV=Cytomegalovirus promoter, BGHp(A)=Bovine Growth Hormone poly-adenylation sequence, fl ori=fl origin of replication, SV40=Simian Virus 40 promoter, Neo=Neomycin resistance marker, Hyg=Hygromycin resistance marker, SV40 p(A)=Simian Virus 40 poly-adenylation sequence, FSH A=Follicle stimulating hormone alpha polypeptide, FSH B=Follicle stimulating hormone beta polypeptide, ST3GAL4=α2,3-sialyltransferase, ST6GAL1=α2,6-sialyltransferase, ColEl=ColEl origin of replication, Amp=ampicillin resistance marker.

Follicle stimulating hormone alpha polypeptide
Accession number AH007338
Nucleotide sequence of FSH alpha SEQ ID NO: 1
```
  1 ATGGATTACT ACAGAAAATA TGCAGCTATC TTTCTGGTCA CATTGTCGGT GTTTCTGCAT

61 GTTCTCCATT CCGCTCCTGA TGTGCAGGAT TGCCCAGAAT GCACGCTACA GGAAAACCCA

121 TTCTTCTCCC AGCCGGGTGC CCCAATACTT CAGTGCATGG GCTGCTGCTT CTCTAGAGCA

181 TATCCCACTC CACTAAGGTC CAAGAAGACG ATGTTGGTCC AAAAGAACGT CACCTCAGAG

241 TCCACTTGCT GTGTAGCTAA ATCATATAAC AGGGTCACAG TAATGGGGGG TTTCAAAGTG

301 GAGAACCACA CGGCGTGCCA CTGCAGTACT TGTTATTATC ACAAATCTTA A
```

Protein sequence of FSH alpha (SEQ ID NO: 5)
```
  1 MDYYRKYAAI FLVTLSVFLH VLHSAPDVQD CPECTLQENP FFSQPGAPIL QCMGCCFSRA

61 YPTPLRSKKT MLVQKNVTSE STCCVAKSYN RVTVMGGFKV ENHTACHCST CYYHKS
```

Follicle stimulating hormone beta polypeptide
Accession number NM_000510
Nucleotide sequence of FSH beta SEQ ID NO: 2
```
  1 ATGAAGACAC TCCAGTTTTT CTTCCTTTTC TGTTGCTGGA AAGCAATCTG CTGCAATAGC

61 TGTGAGCTGA CCAACATCAC CATTGCAATA GAGAAAGAAG AATGTCGTTT CTGCATAAGC

121 ATCAACACCA CTTGGTGTGC TGGCTACTGC TACACCAGGG ATCTGGTGTA TAAGGACCCA

181 GCCAGGCCCA AATCCAGAA ACATGTACC TTCAAGGAAC TGGTATATGA ACAGTGAGA

241 GTGCCCGGCT GTGCTCACCA TGCAGATTCC TTGTATACAT ACCCAGTGGC CACCCAGTGT

301 CACTGTGGCA AGTGTGACAG CGACAGCACT GATTGTACTG TGCGAGGCCT GGGGCCCAGC

361 TACTGCTCCT TTGGTGAAAT GAAAGAATAA
```

Protein sequence of FSH beta (SEQ ID NO: 6)
```
  1 MKTLQFFFLF CCWKAICCNS CELTNITIAI EKEECRFCIS INTTWCAGYC YTRDLVYKDP

61 ARPKIQKTCT FKELVYETVR VPGCAHHADS LYTYPVATQC HCGKCDSDST DCTVRGLGPS

121 YCSFGEMKE
```

Beta-galactoside alpha-2,3-sialyltransferase 4
Accession Number L23767
Nucleotide sequence of ST3GAL4

SEQ ID NO: 3
```
  1 ATGTGTCCTG CAGGCTGGAA GCTCCTGGCC ATGTTGGCTC TGGTCCTGGT CGTCATGGTG

61 TGGTATTCCA TCTCCCGGGA AGACAGGTAC ATCGAGCTTT TTATTTTCC CATCCCAGAG

121 AAGAAGGAGC CGTGCCTCCA GGGTGAGGCA GAGAGCAAGG CCTCTAAGCT CTTTGGCAAC

181 TACTCCCGGG ATCAGCCCAT CTTCCTGCGG CTTGAGGATT ATTTCTGGGT CAAGACGCCA

241 TCTGCTTACG AGCTGCCCTA TGGGACCAAG GGGAGTGAGG ATCTGCTCCT CCGGGTGCTA

301 GCCATCACCA GCTCCTCCAT CCCCAAGAAC ATCCAGAGCC TCAGGTGCCG CCGCTGTGTG

361 GTCGTGGGGA ACGGGCACCG GCTGCGGAAC AGCTCACTGG GAGATGCCAT CAACAAGTAC

421 GATGTGGTCA TCAGATTGAA CAATGCCCCA GTGGCTGGCT ATGAGGGTGA CGTGGGCTCC

481 AAGACCACCA TGCGTCTCTT CTACCCTGAA TCTGCCCACT TCGACCCCAA GTAGAAAAC

541 AACCCAGACA CACTCCTCGT CCTGGTAGCT TTCAAGGCAA TGGACTTCCA CTGGATTGAG

601 ACCATCCTGA GTGATAAGAA GCGGGTGCGA AAGGGTTTCT GGAAACAGCC TCCCCTCATC

661 TGGGATGTCA ATCCTAAACA GATTCGGATT CTCAACCCCT TCTTCATGGA GATTGCAGCT

721 GACAAACTGC TGAGCCTGCC AATGCAACAG CCACGGAAGA TTAAGCAGAA GCCCACCACG

781 GGCCTGTTGG CCATCACGCT GGCCCTCCAC CTCTGTGACT TGGTGCACAT TGCCGGCTTT

841 GGCTACCCAG ACGCCTACAA CAAGAAGCAG ACCATTCACT ACTATGAGCA GATCACGCTC
```

-continued

```
 901 AAGTCCATGG CGGGGTCAGG CCATAATGTC TCCCAAGAGG CCCTGGCCAT TAAGCGGATG

961 CTGGAGATGG GAGCTATCAA GAACCTCACG TCCTTCTGA
```

Protein Sequence of ST3GAL4

(SEQ ID NO: 7)

```
   1 MCPAGWKLLA MLALVLVVMV WYSISREDRY IELFYFPIPE KKEPCLQGEA ESKASKLFGN

61 YSRDQPIFLR LEDYFWVKTP SAYELPYGTK GSEDLLLRVL AITSSSIPKN IQSLRCRRCV

121 VVGNGHRLRN SSLGDAINKY DVVIRLNNAP VAGYEGDVGS KTTMRLFYPE SAHFDPKVEN

181 NPDTLLVLVA FKAMDFHWIE TILSDKKRVR KGFWKQPPLI WDVNPKQIRI LNPFFMEIAA

241 DKLLSLPMQQ PRKIKQKPTT GLLAITLALH LCDLVHIAGF GYPDAYNKKQ TIHYYEQITL

301 KSMAGSGHNV SQEALAIKRM LEMGAIKNLT SF
```

Beta-galactosamide alpha-2,6-sialyltransferase 1
Accession number NM_003032
Nucleotide sequence of ST6GAL1

SEQ ID NO: 4

```
   1 ATGATTCACA CCAACCTGAA GAAAAAGTTC AGCTGCTGCG TCCTGGTCTT TCTTCTGTTT

61 GCAGTCATCT GTGTGTGGAA GGAAAAGAAG AAAGGGAGTT ACTATGATTC CTTTAAATTG

121 CAAACCAAGG AATTCCAGGT GTTAAAGAGT CTGGGGAAAT TGGCCATGGG GTCTGATTCC

181 CAGTCTGTAT CCTCAAGCAG CACCCAGGAC CCCCACAGGG GCCGCCAGAC CCTCGGCAGT

241 CTCAGAGGCC TAGCCAAGGC CAAACCAGAG GCCTCCTTCC AGGTGTGGAA CAAGGACAGC

301 TCTTCCAAAA ACCTTATCCC TAGGCTGCAA AAGATCTGGA AGAATTACCT AAGCATGAAC

361 AAGTACAAAG TGTCCTACAA GGGGCCAGGA CCAGGCATCA AGTTCAGTGC AGAGGCCCTG

421 CGCTGCCACC TCCGGGACCA TGTGAATGTA TCCATGGTAG AGGTCACAGA TTTTCCCTTC

481 AATACCTCTG AATGGGAGGG TTATCTGCCC AAGGAGAGCA TTAGGACCAA GGCTGGGCCT

541 TGGGGCAGGT GTGCTGTTGT GTCGTCAGCG GGATCTCTGA AGTCCTCCCA ACTAGGCAGA

601 GAAATCGATG ATCATGACGC AGTCCTGAGG TTTAATGGGG CACCCACAGC CAACTTCCAA

661 CAAGATGTGG GCACAAAAAC TACCATTCGC CTGATGAACT CTCAGTTGGT TACCACAGAG

721 AAGCGCTTCC TCAAAGACAG TTTGTACAAT GAAGGAATCC TAATTGTATG GGACCCATCT

781 GTATACCACT CAGATATCCC AAAGTGGTAC CAGAATCCGG ATTATAATTT CTTTAACAAC

841 TACAAGACTT ATCGTAAGCT GCACCCCAAT CAGCCCTTTT ACATCCTCAA GCCCCAGATG

901 CCTTGGGAGC TATGGGACAT TCTTCAAGAA ATCTCCCCAG AAGAGATTCA GCCAAACCCC

961 CCATCCTCTG GGATGCTTGG TATCATCATC ATGATGACGC TGTGTGACCA GGTGGATATT

1021 TATGAGTTCC TCCCATCCAA GCGCAAGACT GACGTGTGCT ACTACTACCA GAAGTTCTTC

1081 GATAGTGCCT GCACGATGGG TGCCTACCAC CCGCTGCTCT ATGAGAAGAA TTTGGTGAAG

1141 CATCTCAACC AGGGCACAGA TGAGGACATC TACCTGCTTG GAAAAGCCAC ACTGCCTGGC

1201 TTCCGGACCA TTCACTGCTA A
```

0p-Protein Sequence of ST6GAL1

(SEQ ID NO: 8)

```
   1 MIHTNLKKKF SCCVLVFLLF AVICVWKEKK KGSYYDSFKL QTKEFQVLKS LGKLAMGSDS

61 QSVSSSSTQD PHRGRQTLGS LRGLAKAKPE ASFQVWNKDS SSKNLIPRLQ KIWKNYLSMN

121 KYKVSYKGPG PGIKFSAEAL RCHLRDHVNV SMVEVTDFPF NTSEWEGYLP KESIRTKAGP

181 WGRCAVVSSA GSLKSSQLGR EIDDHDAVLR FNGAPTANFQ QDVGTKTTIR LMNSQLVTTE

241 KRFLKDSLYN EGILIVWDPS VYHSDIPKWY QNPDYNFFNN YKTYRKLHPN QPFYILKPQM

301 PWELWDILQE ISPEEIQPNP PSSGMLGIII MMTLCDQVDI YEFLPSKRKT DVCYYYQKFF

361 DSACTMGAYH PLLYEKNLVK HLNQGTDEDI YLLGKATLPG FRTIHC
```

The invention claimed is:

1. A method of treating infertility, comprising administering a follicle stimulating hormone (FSH) composition at a dose of or equivalent to from 9 to 24 μg FSH to a patient identified prior to treatment as having (i) variant Ser/Ser at position 680 of the FSH receptor and (ii) a serum AMH level of 15.0 to 44.9 pmol/L.

2. The method of claim 1, wherein the method comprises daily administration of the FSH composition.

3. The method of claim 1, wherein the method comprises administering the FSH composition at a dose of or equivalent to from greater than 12 to 24 μg FSH.

4. The method of claim 1, wherein the FSH composition is administered starting on day one of treatment and continuing for from six to sixteen days.

5. The method of claim 1, wherein the FSH is recombinant FSH.

6. The method of claim 1, wherein the FSH is recombinant FSH that includes α2,3-sialylation and α2,6-sialylation.

7. The method of claim 1, wherein the FSH is recombinant FSH that includes α2,3-sialylation and α2,6-sialylation, wherein from 1 to 99% of the total sialylation is α2,6-sialylation and from 99% to 1% of the total sialylation is α2,3-sialylation.

8. The method of claim 1, wherein the FSH is recombinant FSH that includes α2,3-sialylation and α2,6-sialylation, wherein from 1 to 50% of the total sialylation is α2,6-sialylation and from 50% to 99% of the total sialylation is α2,3-sialylation.

9. A method of treating infertility, comprising administering a follicle stimulating hormone (FSH) composition at a dose of or equivalent to from 10 to 12 μg FSH to a patient identified prior to treatment as having (i) variant Asn/Asn or variant Asn/Ser at position 680 of the FSH receptor and (ii) a serum AMR level of 15.0 to 44.9 pmol/L.

10. The method of claim 9, wherein the FSH is recombinant FSH that includes α2,3-sialylation and α2,6-sialylation, wherein from 1 to 50% of the total sialylation is α2,6-sialylation and from 50% to 99% of the total sialylation is α2,3-sialylation.

* * * * *

UNITED STATES PATENT AND TRADEMARK OFFICE
CERTIFICATE OF CORRECTION

PATENT NO. : 11,439,686 B2
APPLICATION NO. : 16/881163
DATED : September 13, 2022
INVENTOR(S) : Arce Sacz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 111 days.

Signed and Sealed this
Fourth Day of February, 2025

Coke Morgan Stewart
*Acting Director of the United States Patent and Trademark Office*

SEQUENCE LISTING

<160> NUMBER OF SEQ ID NOS: 16

<210> SEQ ID NO 1
<211> LENGTH: 351
<212> TYPE: DNA
<213> ORGANISM: Homo sapiens

<400> SEQUENCE: 1

```
atggattact acagaaaata tgcagctatc tttctggtca cattgtcggt gtttctgcat        60
gttctccatt ccgctcctga tgtgcaggat tgcccagaat gcacgctaca ggaaaaccca       120
ttcttctccc agccgggtgc cccaatactt cagtgcatgg gctgctgctt ctctagagca       180
tatcccactc cactaaggtc caagaagacg atgttggtcc aaaagaacgt cacctcagag       240
tccacttgct gtgtagctaa atcatataac agggtcacag taatgggggg tttcaaagtg       300
gagaaccaca cggcgtgcca ctgcagtact tgttattatc acaaatctta a                351
```

<210> SEQ ID NO 2
<211> LENGTH: 390
<212> TYPE: DNA
<213> ORGANISM: Homo sapiens

<400> SEQUENCE: 2

```
atgaagacac tccagttttt cttccttttc tgttgctgga aagcaatctg ctgcaatagc        60
tgtgagctga ccaacatcac cattgcaata gagaagaag aatgtcgttt ctgcataagc        120
atcaacacca cttggtgtgc tggctactgc tacaccaggg atctggtgta taaggaccca       180
gccaggccca aaatccagaa aacatgtacc ttcaaggaac tggtatatga acagtgaga       240 gtgcccggct gtgctcacca tgcagattcc ttgtatacat cccagtggc cacccagtgt       300 cactgtggca gtgtgacag cgacagcact gattgtactg tgcgaggcct ggggcccagc       360
tactgctcct ttggtgaaat gaaagaataa                                        390
```

<210> SEQ ID NO 3
<211> LENGTH: 999
<212> TYPE: DNA
<213> ORGANISM: Homo sapiens

<400> SEQUENCE: 3

```
atgtgtcctg caggctggaa gctcctggcc atgttggctc tggtcctggt cgtcatggtg        60
tggtattcca tctcccggga agacaggtac atcgagcttt ttatttttcc catcccagag       120
aagaaggagc cgtgcctcca gggtgaggca gagagcaagg cctctaagct ctttggcaac       180
tactcccggg atcagcccat cttcctgcgg cttgaggatt attctgggt caagacgcca       240 tctgcttacg agctgcccta tgggaccaag gggagtgagg atctgctcct ccgggtgcta       300
gccatcacca gctcctccat ccccaagaac atccagagcc tcaggtgccg ccgctgtgtg       360
gtcgtgggga acgggcaccg gctgcggaac agctcactgg gagatgccat caacaagtac       420
gatgtggtca tcagattgaa caatgcccca gtggctggct atgagggtga cgtgggctcc       480
aagaccacca tgcgtctctt ctaccctgaa tctgcccact cgaccccaa agtagaaaac       540 aacccagaca cactcctcgt cctggtagct ttcaaggcaa tggacttcca ctggattgag       600
accatcctga gtgataagaa gcgggtgcga aagggttct ggaaacagcc tcccctcatc       660
tgggatgtca atcctaaaca gattcggatt ctcaaccct tcttcatgga gattgcagct       720
gacaaactgc tgagcctgcc aatgcaacag ccacggaaga ttaagcagaa gcccaccacg       780
ggcctgttgg ccatcacgct ggccctccac ctctgtgact tggtgcacat tgccggcttt       840
```

```
ggctacccag acgcctacaa caagaagcag accattcact actatgagca gatcacgctc    900
aagtccatgg cggggtcagg ccataatgtc tcccaagagg ccctggccat taagcggatg    960
ctggagatgg gagctatcaa gaacctcacg tccttctga                          999

<210> SEQ ID NO 4
<211> LENGTH: 1221
<212> TYPE: DNA
<213> ORGANISM: Homo sapiens

<400> SEQUENCE: 4
atgattcaca ccaacctgaa gaaaaagttc agctgctgcg tcctggtctt tcttctgttt     60
gcagtcatct gtgtgtggaa ggaaaagaag aaagggagtt actatgattc ctttaaattg    120
caaaccaagg aattccaggt gttaaagagt ctggggaaat tggccatggg gtctgattcc    180
cagtctgtat cctcaagcag caccccaggac ccccacaggg gccgccagac cctcggcagt    240
ctcagaggcc tagccaaggc caaaccagag gcctccttcc aggtgtggaa caaggacagc    300
tcttccaaaa accttatccc taggctgcaa aagatctgga gaattaccct aagcatgaac    360
aagtacaaag tgtcctacaa ggggccagga ccaggcatca agttcagtgc agaggccctg    420
cgctgccacc tccgggacca tgtgaatgta tccatggtag aggtcacaga ttttcccttc    480
aatacctctg aatgggaggg ttatctgccc aaggagagca ttaggaccaa ggctgggcct    540
tggggcaggt gtgctgttgt gtcgtcagcg ggatctctga agtcctccca actaggcaga    600
gaaatcgatg atcatgacgc agtcctgagg tttaatgggg cacccacagc caacttccaa    660
caagatgtgg gcacaaaaac taccattcgc ctgatgaact ctcagttggt taccacagag    720
aagcgcttcc tcaaagacag tttgtacaat gaaggaatcc taattgtatg ggacccatct    780
gtataccact cagatatccc aaagtggtac cagaatccgg attataattt ctttaacaac    840
tacaagactt atcgtaagct gcaccccaat cagccctttt acatcctcaa gccccagatg    900
ccttgggagc tatgggacat tcttcaagaa atctccccag aagagattca gccaaacccc    960
ccatcctctg ggatgcttgg tatcatcatc atgatgacgc tgtgtgacca ggtggatatt   1020
tatgagttcc tcccatccaa cgcaagact gacgtgtgct actactacca gaagttcttc   1080
gatagtgcct gcacgatggg tgcctaccac ccgctgctct atgagaagaa tttggtgaag   1140
catctcaacc agggcacaga tgaggacatc tacctgcttg aaaagccac actgcctggc   1200 ttccggacca ttcactgcta a                                             1221

<210> SEQ ID NO 5
<211> LENGTH: 116
<212> TYPE: PRT
<213> ORGANISM: Homo sapiens

<400> SEQUENCE: 5

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
        50                  55                  60

Leu Arg Ser Lys Lys Thr Met Leu Val Gln Lys Asn Val Thr Ser Glu
65                  70                  75                  80
```

```
Ser Thr Cys Cys Val Ala Lys Ser Tyr Asn Arg Val Thr Val Met Gly
            85                  90                  95

Gly Phe Lys Val Glu Asn His Thr Ala Cys His Cys Ser Thr Cys Tyr
            100                 105                 110

Tyr His Lys Ser
        115

<210> SEQ ID NO 6
<211> LENGTH: 129
<212> TYPE: PRT
<213> ORGANISM: Homo sapiens

<400> SEQUENCE: 6

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Lys
50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
            85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
            115                 120                 125

Glu

<210> SEQ ID NO 7
<211> LENGTH: 332
<212> TYPE: PRT
<213> ORGANISM: Homo sapiens

<400> SEQUENCE: 7

Met Cys Pro Ala Gly Trp Lys Leu Leu Ala Met Leu Ala Leu Val Leu
1               5                   10                  15

Val Val Met Val Trp Tyr Ser Ile Ser Arg Glu Asp Arg Tyr Ile Glu
            20                  25                  30

Leu Phe Tyr Phe Pro Ile Pro Glu Lys Lys Glu Pro Cys Leu Gln Gly
            35                  40                  45

Glu Ala Glu Ser Lys Ala Ser Lys Leu Phe Gly Asn Tyr Ser Arg Asp
            50                  55                  60

Gln Pro Ile Phe Leu Arg Leu Glu Asp Tyr Phe Trp Val Lys Thr Pro
65                  70                  75                  80

Ser Ala Tyr Glu Leu Pro Tyr Gly Thr Lys Gly Ser Glu Asp Leu Leu
            85                  90                  95

Leu Arg Val Leu Ala Ile Thr Ser Ser Ile Pro Lys Asn Ile Gln
            100                 105                 110

Ser Leu Arg Cys Arg Arg Cys Val Val Gly Asn Gly His Arg Leu
            115                 120                 125

Arg Asn Ser Ser Leu Gly Asp Ala Ile Asn Lys Tyr Asp Val Val Ile
            130                 135                 140
```

-continued

Arg Leu Asn Asn Ala Pro Val Ala Gly Tyr Glu Gly Asp Val Gly Ser
145                 150                 155                 160

Lys Thr Thr Met Arg Leu Phe Tyr Pro Glu Ser Ala His Phe Asp Pro
            165                 170                 175

Lys Val Glu Asn Asn Pro Asp Thr Leu Leu Val Leu Val Ala Phe Lys
                180                 185                 190

Ala Met Asp Phe His Trp Ile Glu Thr Ile Leu Ser Asp Lys Lys Arg
            195                 200                 205

Val Arg Lys Gly Phe Trp Lys Gln Pro Pro Leu Ile Trp Asp Val Asn
        210                 215                 220

Pro Lys Gln Ile Arg Ile Leu Asn Pro Phe Phe Met Glu Ile Ala Ala
225                 230                 235                 240

Asp Lys Leu Leu Ser Leu Pro Met Gln Gln Pro Arg Lys Ile Lys Gln
                245                 250                 255

Lys Pro Thr Thr Gly Leu Leu Ala Ile Thr Leu Ala Leu His Leu Cys
            260                 265                 270

Asp Leu Val His Ile Ala Gly Phe Gly Tyr Pro Asp Ala Tyr Asn Lys
                275                 280                 285

Lys Gln Thr Ile His Tyr Tyr Glu Gln Ile Thr Leu Lys Ser Met Ala
        290                 295                 300

Gly Ser Gly His Asn Val Ser Gln Glu Ala Leu Ala Ile Lys Arg Met
305                 310                 315                 320

Leu Glu Met Gly Ala Ile Lys Asn Leu Thr Ser Phe
                325                 330

<210> SEQ ID NO 8
<211> LENGTH: 406
<212> TYPE: PRT
<213> ORGANISM: Homo sapiens

<400> SEQUENCE: 8

Met Ile His Thr Asn Leu Lys Lys Phe Ser Cys Cys Val Leu Val
1               5                   10                  15

Phe Leu Leu Phe Ala Val Ile Cys Val Trp Lys Glu Lys Lys Lys Gly
            20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Lys Asn Leu Ile Pro Arg Leu Gln Lys Ile
            100                 105                 110

Trp Lys Asn Tyr Leu Ser Met Asn Lys Tyr Lys Val Ser Tyr Lys Gly
        115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
            180                 185                 190

```
Leu Lys Ser Ser Gln Leu Gly Arg Glu Ile Asp Asp His Asp Ala Val
            195                 200                 205

Leu Arg Phe Asn Gly Ala Pro Thr Ala Asn Phe Gln Gln Asp Val Gly
        210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
            260                 265                 270

Pro Asp Tyr Asn Phe Phe Asn Asn Tyr Lys Thr Tyr Arg Lys Leu His
        275                 280                 285

Pro Asn Gln Pro Phe Tyr Ile Leu Lys Pro Gln Met Pro Trp Glu Leu
    290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Met Met Thr Leu Cys Asp
                325                 330                 335

Gln Val Asp Ile Tyr Glu Phe Leu Pro Ser Lys Arg Lys Thr Asp Val
            340                 345                 350

Cys Tyr Tyr Tyr Gln Lys Phe Phe Asp Ser Ala Cys Thr Met Gly Ala
        355                 360                 365

Tyr His Pro Leu Leu Tyr Glu Lys Asn Leu Val Lys His Leu Asn Gln
    370                 375                 380

Gly Thr Asp Glu Asp Ile Tyr Leu Leu Gly Lys Ala Thr Leu Pro Gly
385                 390                 395                 400

Phe Arg Thr Ile His Cys
                405

<210> SEQ ID NO 9
<211> LENGTH: 39
<212> TYPE: DNA
<213> ORGANISM: Artificial Sequence
<220> FEATURE:
<223> OTHER INFORMATION: PCR primer FSHa-fw

<400> SEQUENCE: 9
ccaggatccg ccaccatgga ttactacaga aaaatatgc                              39

<210> SEQ ID NO 10
<211> LENGTH: 31
<212> TYPE: DNA
<213> ORGANISM: Artificial Sequence
<220> FEATURE:
<223> OTHER INFORMATION: PCR primer FSHa-rev

<400> SEQUENCE: 10
ggatggctag cttaagattt gtgataataa c                                      31

<210> SEQ ID NO 11
<211> LENGTH: 35
<212> TYPE: DNA
<213> ORGANISM: Artificial Sequence
<220> FEATURE:
<223> OTHER INFORMATION: PCR primer FSHb-fw

<400> SEQUENCE: 11
ccaggcgcgc caccatgaag acactccagt ttttc                                  35
```

```
<210> SEQ ID NO 12
<211> LENGTH: 36
<212> TYPE: DNA
<213> ORGANISM: Artificial Sequence
<220> FEATURE:
<223> OTHER INFORMATION: PCR primer FSHb-rev

<400> SEQUENCE: 12
ccgggttaac ttattattct ttcatttcac caaagg                                     36

<210> SEQ ID NO 13
<211> LENGTH: 37
<212> TYPE: DNA
<213> ORGANISM: Artificial Sequence
<220> FEATURE:
<223> OTHER INFORMATION: PCR primer 2,3STfw

<400> SEQUENCE: 13
ccaggatccg ccaccatgtg tcctgcaggc tggaagc                                    37

<210> SEQ ID NO 14
<211> LENGTH: 35
<212> TYPE: DNA
<213> ORGANISM: Artificial Sequence
<220> FEATURE:
<223> OTHER INFORMATION: PCR primer 2,3STrev

<400> SEQUENCE: 14 ttttttctt aagtcagaag gacgtgaggt tcttg                                       35

<210> SEQ ID NO 15
<211> LENGTH: 36
<212> TYPE: DNA
<213> ORGANISM: Artificial Sequence
<220> FEATURE:
<223> OTHER INFORMATION: PCR primer 2,6STfw

<400> SEQUENCE: 15
ccaggatccg ccaccatgat tcacaccaac ctgaag                                     36

<210> SEQ ID NO 16
<211> LENGTH: 32
<212> TYPE: DNA
<213> ORGANISM: Artificial Sequence
<220> FEATURE:
<223> OTHER INFORMATION: PCR primer 2,6STrev

<400> SEQUENCE: 16
tttttttctt aagttagcag tgaatggtcc gg                                         32
```